US006410687B1

(12) United States Patent
Vale et al.

(10) Patent No.: US 6,410,687 B1
(45) Date of Patent: Jun. 25, 2002

(54) POLYPEPTIDES FOR THE DETECTION OF MICROTUBULE DEPOLYMERIZATION INHIBITORS

(75) Inventors: Ronald D. Vale; James J. Hartman, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/291,170

(22) Filed: Apr. 13, 1999

Related U.S. Application Data

(60) Provisional application No. 60/081,734, filed on Apr. 14, 1998.

(51) Int. Cl.[7] .......................... C07K 1/00; C07K 14/00; C07K 17/00; C07K 16/00; A61K 35/14

(52) U.S. Cl. .................... 530/350; 530/386; 530/387.1

(58) Field of Search ................................ 530/350, 386, 530/387.1

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,458,066 A | 7/1984 | Caruthers et al. |
| 5,010,175 A | 4/1991 | Rutter et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,541,061 A | 7/1996 | Fodor et al. |
| 5,549,974 A | 8/1996 | Holmes |
| 5,559,410 A | 9/1996 | Papazian et al. |
| 5,569,588 A | 10/1996 | Ashby et al. |
| 5,576,220 A | 11/1996 | Hudson et al. |
| 5,585,639 A | 12/1996 | Dorsel et al. |
| 5,593,853 A | 1/1997 | Chen et al. |

FOREIGN PATENT DOCUMENTS

| | | |
|---|---|---|
| WO | WO 91/19735 | 12/1991 |
| WO | WO 92/00091 | 1/1992 |
| WO | WO 93/20242 | 10/1993 |
| WO | WO 97/00271 | 1/1997 |

OTHER PUBLICATIONS

Amino acid database, Accession #O61577, 1998.*
Amino acid/ nucliec acid database, Accession #W34919, 1996.*
Amino acid/ nucleic acid database, Accession AF052191, 1998.*
McNally and Vale. Identification of katanin, an ATPase that severs and disassembles stable microtubules. Cell 75(3):419–29, 1993.*
Vale and Kreis, 1993, Guidebook to the Cytoskeletal and Motor Proteins, NY, Oxford University Press.
Alberts et al., 1994, Molecular Biology of the Cell, pp. 788–858.
Goldstein (1993) "With Apologies to Scheherazade: Tails of 1001 Kinesin Motors," Ann. Rev. Genetics 27:319–351;.
Mooseker and Cheney (1995) "Unconventional Myosins, "Annu. Rev. Cell Biol. 11:633–675;.
Turner et al.(1996) "Kinesin Movement on Glutaraldehyde–Fixed Microtubules," Anal. Biochem. 242(1):20–25.
Gittes et al. (1996) "Directional Loading of the Kinesin Motor Molecule as it Buckles a Microtubule," Biophys. J. 70(1):418–29.
Shirakawa et al. (1995) "The Mode of ATP–Dependent Microtubule–Kinesin Sliding in the Auxotonic Condition," J. Exp. Biol. 198:1809–15.
Winkelkmann et al. (1995) "Flexibility of Mysoin Attachment to Surfaces Influences F–Actin Motion," Biophys. J. 68:2444–53.
Winkelkmann et al. (1995) "Motility Assays Using Myosin Attached to Surfaces through Specific Binding to Monoclonal Antibodies," Biophys. J. 68:72S.
Batzer et al. (1991) "Enhanced evolutionary PCR using oligonucleotides with inosine at the 3–terminus," Nucl. Acid Res. 19:5081.
Ohtsuka et al. (1985) "An Alternative Approach to Deoxyoligonucleotides as Hybridization Probes by Insertion of Deoxyinosine at Ambiguous Codon Positions," J. Biol. Chem. 260:2605–2608.
Rossolini et al. (1994) "Use of deoxyinosine–containing primers vs degenerate primers for polymerase chain reaction based on ambiguous sequence information," Mol. Cell. Probes 8:91–98.
Smith and Waterman (1981) "Comparison of Biosequences," Adv. Appl. Math. 2:482.
Needleman & Wunsch (1970) "A General Method Applicable to the Search for Similarities in the Amino Acid Sequence of Two Proteins," J. Mol. Biol. 48:443.

(List continued on next page.)

Primary Examiner—Anthony C. Caputa
Assistant Examiner—Alana M. Harris
(74) Attorney, Agent, or Firm—Medlen & Carroll, LLP

(57) ABSTRACT

This invention provides methods for the screening and identification of agents having potent effects on the progression of the cell cycle. In one embodiment, the methods involve contacting a polymerized microtubule with a microtubule severing protein or a microtubule depolymerizing protein in the presence of an ATP or a GTP and a test agent; and detecting the formation of tubulin monomers, dimers or oligomers. The p60 subunit of katanin provides a particularly preferred microtubule severing protein possessing both ATPase and microtubule severing activities.

4 Claims, 7 Drawing Sheets

OTHER PUBLICATIONS

Pearson & Lipman (1988) "Improved tools for biological sequence comparison," Proc. Natl. Acad. Sci. USA 85:2444.

Ausubel et al. (eds.), *Current Protocols in Molecular Biology*, John Wiley & Sons, Inc., NY, 1994.

Feng & Doolittle (1987) "Progressive Sequence Alignment as a Prerequistite to Correct Phylogenetic Trees," J. Mol. Evol. 25:351–360.

Higgins & Sharp (1989) "Fast and sensitive multiple sequence alignments on a microcomputer," CABIOS 5:151–153.

Altschul et al. (1990) "Basic Local Alignment Search Tool," J. Mol. Biol. 215:403–410.

Henikoff & Henikoff (1989) "Amino acid substitution matrices from protein blocks," Proc. Natl. Acad. Sci. USA 89:10915.

Karlin & Altschul (1993) "Applications and statistics for multiple high–scoring segments in molecular sequences," Proc. Natl. Acad. Sci. USA 90:5873–5787.

Tijssen (1993) in *Laboratory Techniques in Biochemistry and Molecular Biology—Hybridization with Nucleic Acid Probes*, Part I, Chapter 2, A overview of principles of hybridization and the strategy of nucleic acid probe assays, Elsevier, NY.

Sambrook et al. (1989) *Molecular Cloning, A Laboratory Manual*, 2nd ed., vols. 1–3, Cold Spring Harbor Laboratory, Cold Spring Harbor Press, NY.

Stites and Terr (1991) in *Basic and Clinical Immunology*, 7th ed., Appleton & Lange, Norwalk, Connecticut.

Maggio (1980) in *Enzyme Immunoassay*, CRC Press, Boca Raton, FL.

Tijssen (1985) "Practice and Theory of Enzyme Immunoassays," in *Laboratory Techniques in Biochemistry and Molecular Biology*, Elsevier Science Publishers, B.V. Amsterdam.

Kodama et al. (1986) "The Initial Phosphate Burst in AtP Hydrolysis by Myosin and Subfragment–1 as Studied by a Modified Malachite Green Method for Determination of Inorganic Phosphate," J. Biochem. 99:1465–1472.

Collioud et al. (1993) "Oriented and Covalent Immobilization of Target Molecules to Solid Supports: Synthesis and Application of a Light–Activatable and Thiol–Reactive Cross–Linking Reagent," Bioconjugate Chem. 4:528–536.

Schuhmann et al. (1991) "Immobilization of Enzymes on Langmuir–Blodgett Films via a Membrane–Bound Receptor. Possible Applications for Amperometric Biosensors," Adv. Mater. 3:388–391.

Lu et al. (1995) "Oriented Immobilization of Fab' Fragments on Silica Surfaces," Anal. Chem. 67:83–87.

Iwane et al. (1997) "Myosin Subfragment–1 Is Fully Equipped with Factors Essential for Motor Function," Biophys. Biochem. Res. Comm. 230:76–80.

Ng et al. (1995) "Engineering Protein—Lipid Interactions: Targeting of Histidine–Tagged Proteins to Metal–Chelating Lipid Monolayers," Langmuir 11:4048–4055.

Schmitt et al. (1996) Specific Proteins Docking to Chelator Lipid Monolayers Monitored by FT–IR Spectroscopy at the Air–Water Inferface; Agnew. Chem. Int. Ed. Engl. 35:317–320.

Frey et al. (1996) "Two–dimensional protein crystallization via metal–ion coordination by naturally occurring surface histidines," Proc. Natl. Acad. Sci. USA 93:4937–4941.

Kubalek et al. (1994) "Two–Dimensional Crystallization of Histidine–Tagged, HIV–1 Reverse Transcriptase Promoted by a Novel Nickel–Chelating Lipid," J. Struct. Biol. 113:117–123.

Sigal et al. (1996) "A Self–Assembled Monolayer for the Binding and Study of Histidine–Tagged Proteins by Surface Plasmon Resonance," Anal. Chem. 68:490–497.

Gallop et al. (1994) "Applications of Combinatorial Technologies to Drug Discovery. 1. Background and Peptide Combinatorial Libraries," J. Med. Chem. 37(9):1233–1251.

Furka (1991) "General method for rapid synthesis of multicomponent peptide mixtures," Int. J. Pept. Prot. Res. 37:487–493.

Houghten et al. (1991) "Generation and use of synthetic peptide combinatorial libraries for basic research and drug discovery," Nature 354:84–88.

DeWitt et al. (1993) "'Diversomers': An approach to non-peptide, nonoligomeric chemical diversity," Proc. Natl. Acad. Sci. USA 90:6909–6913.

Hagihara et al. (1992) "Vinylogous Polypeptides: An Alternative Peptide Backbone," J. Amer. Chem. Soc. 114:6568.

Hirschmann et al. (1992) "Nonpeptidal Peptidomimetics with a $\beta$–D–Glucose Scaffolding. A Partial Somatostatin Agonist Bearing a Close Structural Relationship to a Potent, Selective Substance P Antagonist," J. Amer. Chem. Soc. 114:9217–9218.

Chen et al. (1994) "'Analogous" Organic Synthesis of Small–Compound Libraries: Validiation of Combinatorial Chemistry in Small–Molecule Synthesis,'J. Amer. Chem. Soc. 116:2661.

Cho et al. (1993) "An Unnatural Biopolymer," Science 261:1303.

Campbell et al. (1994) "Phosphonate Ester Synthesis Using a Modified Mitsunobu Condensation," J. Org. Chem. 59:658.

Gordon et al. (1994) "Applications of Combinatorial Technologies to Drug Discovery. 2. Combinatorial Prgamoc Synthesis, Library Screening Strategies, and Future Directions." J. Med. Chem. 37:1386.

Vaughan et al. (1996) "Human Antibodies with Sub–nanomolar Affinities Isolated from a Large Non–immunized Phage Display Library," Nature Biotechnology 14(3):309–314.

Liang et al. (1996) "Parallel Synthesis and Screening of a Solid Phase Carbohydrate Library," Science 274:1520–1522.

Baum (1993) "Solid–phase synthesis of benzodiazepines," C&EN, Jan. 18, pp. 33–34.

Morejohn et al. (1985) "Inhibition of Plant Cell Proteolytic Activities that Degrade Tubulin," Cell Biol. Int. Rep. 9(9):849–857.

Bokros et al. (1993) "Characterization of the Reversible Taxol–Induced Polymerization of Plant Tubulin into Microtubules," Biochem. 32(13):3437–3447.

Hyman et al. (1991) "Preparation of Modified Tubulins," Meth. Enzymol. 196:478–485.

Belmont et al. (1990) "Real–Time Visualization of Cell Cycle–Dependent Changes in Microtubule Dynamics in Cytoplasmic Extracts," Cell 62:579–589.

Walczak et al. (1996) "XKCM1: A Xenopus Kinesin–Related Protein That Regulates Microtubule Dynamics during Mitotic Spindle Assembly," Cell 84:37–47.

Vale (1991) "Severing of Stable Microtubules by a Mitotically Activated Protein in Xenopus Egg Extracts," Cell 64:827–839.

Shiina et al. (1994) "Microtubule Severing by Elongation Factor 1α," Science 266:282–285.

Shiina et al. (1992) "A novel homo–oligomeric protein responsible for an MPF–dependent microtubule–severing activity," EMBO J. 11:4723–4731.

McNally and Vale (1993) "Identification of Katanin, an ATPase That Severs and Disassembles Stable Microtubules," Cell 75:419–429.

McNally et al. (1996) "Katanin, the microtuble–severing ATPase, is concentrated at centrosomes," J. Cell Sci. 109:561–567.

Mitchison (1989) "Polewards Microtubule Flux in the Mitotic Spindle: Evidence from Photoactivation of Fluorescense," J. Cell Biol. 109:637–652.

Zheng et al. (1995) "Nucleation of microtubule assembly by a γ–tubulin–containing ring complex," Nature 378:578–583.

Moritz et al. (1995) "Microtubule nucleation by γ–tubulin–containing rings in the centrosome," Nature 378:638–640.

Kitanishi–Yumura et al. (1987) "Reorganization of Microtubules During Mitosis in Dictyostelium: Dissociation From MTOC and Selective Assembly/Disassembly In Situ," Cell Motil. Cytoskeleton 8:106–117.

Keating (1997) "Microtubule release from the centrosome," Proc. Natl. Acad. Sci. USA 94:5078–5083.

Zhai et al. (1996) "Microbutule Dynamics at the $G_2$/M Transition: Abrupt Breakdown of Cytoplasmic Microtubules at Nuclear Envelope Breakdown and Implications for Spindle Morphogenesis," J. Cell Biol. 135:201–214.

Gradin et al.(1998) "Regulation of Microtubule Dynamics by Extracellular Signals: cAMP–dependent Protein Kinase Switches Off the Activity of Oncoprotein 18 in Intact Cells," J. Cell Biol. 140(1):131–141.

Andersen et al. (1997) "Mitotic chromatin regulates phosphorylation of Stathmin/Op18," Nature 389:640–643.

Larsson et al. (1997) "Control of Microtubule Dynamics by Oncoprotein 18: Dissection of the Regulatory Role of Multisite Phosphorylation during Mitosis," Mol. Cell. Biol. 17(9):5530–5539.

Belmont et al. (1996) "Identification of a Protein That Interacts with Tubulin Dimers and Increases the Catastrophe Rate of Microtubules," Cell 84(4):623–631.

Heusele et al. (1987) "Is micotubule assembly a biphasic process?" Eur. J. Biochem. 165:613–620.

Molecular Probes Handbook Catalogue Nos. A–47, A–50, T–53, B–153, P–65, D–3923.

Stryer (1978) "Fluorescence Energy Transfer as a Spectroscopic Ruler," Ann. Rev. Biochem. 47:819–846.

Taylor et al. (1981) "Detection of Actin Assembly by Fluorescence Energy Transfer," J. Cell Biol. 89:362–367.

Yamamoto et al. (1982) "Mechanism of Interaction of Dictyostelium Severin with Actin Filaments," J. Cell Biol. 95:711–719.

Kishino and Yanigida (1988) "Force measurements by micromanipulation of a single actin filament by glass needles," Nature 344:74–76.

Gupta et al. (1998) "Optical Amplification of Ligand–Receptor Binding Using Liquid Crystals," Science 279:2077–2080.

Barany and Merrifield, Solid–Phase Peptide Synthesis, pp. 3–284 in *The peptides: Analysis, Synthesis, Biology, vol. 2: Special methods in Peptide Synthesis, Part A*.

Merrifield et al. (1963) "Solid Phase Peptide Synthesis. I. The Synthesis of a Tetrapeptide," J. Am. Chem. Soc. 85:2149–2156.

Stewart et al. (1984) Solid Phase Peptide Synthesis, 2nd ed., Pierce Chem. Co., Rockford, IL.

Narang et al. (1979) "Improved Phosphotriester Method for the Synthesis of Gene Fragments," Meth. Enzymol. 68:90–99.

Brown et al. (1979) "Chemical Synthesis and Cloning of a Tyrosine tRNA Gene," Meth. Enzymol. 68:109–151.

Beaucage et al. (1981) "Deoxynucleoside Phosphoramidites—A New Class of Key Intermediates for Deoxypolynucleotide Synthesis," Tetra. Lett. 22:1859–1862.

Scopes (1982) Protein Purification, Principles and Practice, 2nd Ed., Springer–Verlag, NY.

Deutscher (1990) Meth. Enzymol., vol. 182: Guide to Protein Purification, Academic Press, Inc., NY.

Debinski et al. (1993) "A Wide Range of Human Cancers Express Interleukin 4 (IL–4) Receptors That Can Be Targeted with Chimeric Toxin Composed of IL4 and Pseudomonas Exotoxin," J. Biol. Chem. 268:14065–14070.

Kreitman and Pastan (1993) "Purification and Characterization of IL6–$PE^{4E}$, a Recombinant Fusion of Interleukin 6 with Pseudomonas Exotoxin," Bioconjug. Chem. 4:581–585.

Buchner et al. (1992) "A Method for Increasing the Yield of Property Folded Recombinant Fusion Proteins: Single–Chain Immunotoxins from Renaturation of Bacterial Inclusion Bodies".

Confalonieri et al. (1995) "A 200–amino acid ATPase module in search of a basic function," BioEssays 17:639–650.

Walker et al. (1982) "Distantly related sequnces in the α– and β–subunits of ATP synthase, myosin, kinases and other ATP–requiring enzymes and a common nucleotide binding fold," EMBO J. 1:945–951.

Clark–Maguire et al. (1994) "mei–1, a Gene Required for Meiotic Spindle Formation in *Caenorhabditis elegans*, Is a Member of a Family of ATPases," Genetics 136:533–546.

Clark–Maguire et al. (1994) "Localization of the mei–1 Gene Product of *Caenorhabditis elegans*, a Meiotic–specific Spindle Component," J. Cell Biol. 126:199–209.

Komachi et al. (1994) "The WD repeats of Tup1 interact with the homeo domain protein α2," Genes Dev. 8:2857–2867.

Wall et al. (1995) "The Structure of the G Protein Heterotrimer $G_{i\alpha 1}\beta_1\gamma_2$," Cell 83:1047–1058.

Heuser (1980) "Protocol for 3–D Visualization of Molecules on Mica via the Quick–Freeze, Deep–Etch Technique," J. Electron Microsc. Technique 13:244–263.

Heuser (1983) "Procedure for Freeze–drying Molecules Adsorbed to Mica Flakes," J. Mol. Biol. 169:155–195.

Hanson et al.(1997) "Structure and Conformational Changes in NSF and Its Membrane Receptor Complexes Visualized by Quick–Freeze/Deep–Etch Electron Microscopy," Cell 90:523–535.

Lin et al. (1995) "Malignant Transformation of Human Fibroblast Strain MSU–1.1 by v–fes Requires an Additional Genetic Change," Int. J. Cancer 63:140–147.

Butner and Kirschner (1991) "Tau Protein Binds to Microtubules through A Flexible Array of Distributed Weak Sites," J. Cell Biol. 115:717–730.

Noble et al. (1989) "The Microtubule Binding Domain of Microtubule–associated Protein MAP1B Contains a Repeated Sequence Motif Unrelated to that of MAP2 and Tau," J.Cell Biol. 109:3367–3376.

Peters et al. (1992) "Ubiquitous Soluble $Mg^{2+}$–ATPase Complex," J. Mol. Biol. 223:557–571.

Morgan et al. (1994) "The ATPase Activity of N–Ethylmaleimide–sensitive Fusion Protein (NSF) Is Regulated by Soluble NSF Attachment Proteins," J. Biol. Chem. 269:29347–29350.

Gilbert et al. (1993) "Expression, Purification, and Characterization of the Drosophila Kinesin Motor Domain Produced in *Escherichia coli*," Biochem. 32:4677–4684.

Lynch et al. (1986) "ATPase Activities and Actin–binding Properties of Subfragments of Acanthamoeba Mysoin IA," J. Biol. Chem. 261:17156–17162.

Tuma and Collins (1994) "Activation of Dynamin GTPase Is a Result of Positive Cooperativity," J. Biol. Chem. 269:30842–30847.

Warnock et al. (1996) "Dynamic Self–assembly Stimultes Its GTPase Activity," J. Biol. Chem. 271:22310–22314.

Hanson et al. (1995) "The N–Ethylmaleimide–sensitive Fusion Protein and α–SNAP Induce a Conformational Change in Syntaxin," J. Biol. Chem. 270:16955–16961.

Hayashi et al. (1995) "Disassembly of the reconstituted synaptic vesicle membrane fusion complex in vitro," EMBO J. 14:2317–2325.

Sondek et al. (1996) "Crystal structure of a $G_A$ protein βγ dimer at 2.1Å resolution," Nature 379:369–374.

Komachi and Johnson (1997) "Residues in the WD Repeats of Tup1 Required for Interaction with α2," Mol. Cell. Biol. 17:6023–6028.

Gaudet et al. (1996) "Crystal Structure at 2.4 Å Resolution of the Complex of Transducin βγ and Its Regulator, Phosducin," Cell 87:577–588.

Oegema et al. (1995) "The Cell Cycle–dependent Localization of the CP190 Centrosomal Protein is Determined by the Coordinate Action of Two Separable Domains," J. Cell Biol. 131:1261–1273.

Iwamatsu (1992) "S–Carboxymethylation of proteins transferred onto polyvinylidene difluoride membranes followed by in situ protease digestion and amino acid microsequenceing," Electrophoresis 13:142–147.

Wright et al. (1991) "Subcellular Localization and Sequence of Sea Urchin Kinesin Heavy Chain: Evidence for its Association with Membranes in the Mitotic Apparatus and Interphase Cytoplasm," J. Cell Biol. 113:817–833.

Apte and Siebert (1993) "Anchor–Ligated cDNA Libraries: A Technique for Generating a cDNA Library for the Immediate Cloning of the 5' Ends of mRNAs," Biotechniques 15:890–893.

Harlow and Lane, *Antibodies: A Laboratory Manual*, Cold Spring Harbor Laboratory Press, Cold Spring Harbor, NY, 1988.

Luckow et al. (1993) "Efficient Generation of Infectious Recombinant Baculoviruses by Site–Specific Transposon–Mediated Insertion of Foreign Genes into a Baculovirus Genome Propagated in *Escherichia coli*," J. Virology 67:4566–4579.

Miller et al. (1990) "Use of Actin Filament and Microtubule Affinity Chromatography to Identify Proteins That Bind to the Cytoskeleton," Meth. Enzymol. 196:303–319.

Williams and Lee (1982) "Preparation of Tubulin from Brain," Meth. Enzymol. 85B:376–385.

Hackney (1988) "Kinesin ATPase: Rate–limiting ADP release," Proc. Natl. Acad. Sci. USA 85:6314–6318.

Genbank Accession No. 061577.

Genbank Accession No. W34919.

Genbank Accession No. AF052191.

Hartman et al. (1995) "ATPase Activity and Cloning of the Putative ATP Binding Subunit of the Microtubule Severing Protein, Katanin," Mol. Biol. of the Cell, Supplement to vol. 6, Abstract 1493.

Mandel et al. (1994) "ATP depletion: a novel method to study junctional properties in epithelial tissues, II. Internalization of $Na^+$, $K^+$–ATPase and E–cadherin," J. Cell Science 107:3315–03324.

Ramirez et al. (1997) "Disruption of microtubule assembly and spindle formation as a mechanism for the induction of aneuploid cells by sodium arsenite and vanadium pentoxide," Mut. Res. 386:291–298.

* cited by examiner

```
  1    MSVDEICENTKMGREYALLGNYETSLVYYQGVLQQIQKLL
 41    TSVHEPQRKHQWQTIRQELSQEYEHVKNITKTLNGFKSEP
 81    AAPEPAPNHRAAPFSHHQHAAKPAAAEPARDPDVWPPPTP
121    VDHRPSPPYQRAARKDPPRRSEPSKPANRAPGNDRGGRGP
161    SDRRGDARSGGGGRGGARGSDKDKNRGGKSDKDKKAPSGE
201    EGDEKKFDPAGYDKDLVENLERDIVQRNPNVHWADIAGLT
241    EAKRLLEEAVVLPLWMPDYFKGIRRPWKGVLMVGPPGTGK
281    TMLAKAVATECGTTFFNVSSASLTSKYHGESEKLVRLLFE
321    MARFYAPSTIFIDEIDSICSKRGTGSEHEASRRVKSELLI
361    QMDGVSGPSAGEESSKMVMVLAATNFPWDIDEALRRRLEK
401    RIYIPLPEIDGREQLLRINLKEVPLADDIDLKSIAEKMDG
441    YSGADITNVCRDASMMAMRRRIQGLRPEEIRHIPKEELNQ
481    PSTPADFLLALQKVSKSVGKEDLVKYMAWMEEFGSV
```

FIG. 1A

```
p60    231  VHWADIAGLTEAKRLLEEAVVLPLWMPDYFKGIRRPW.KGVLMVGPPGTG
mei-1  190  MSLDDIIGMHDVKQVLHEAVTLPLLVPEFFQGLRSPW.KAMVLAGPPGTG
Sug1p  145  STYDMVGGLTKQIKEIKEVIELPVKHPELFESLGIAQPKGVILYGPPGTG
ftsH   149  TTFADVAGCDEAKEEVAELVEY.LREPSRFQKLGGKIPKGVLMVGPPGTG
Pas1p  694  IKWGDIGALANAKDVLLETLEWPTKYEPIFVNCPLRLRSGILLYGYPGCG
NSF    224  EKMGIGGLDDEFSDIFRRAFASRVFPPEIVEQMGCKHVKGILLYGPPGCG p60    280  KTMLAKAVATECGTTFFN.VSSASLTSKYHGESEKLVRLLFEMARFYAP.
mei-1  239  KTLIARAIASESSSTFFT.VSSTDLSSKWRGDSEKIVRLLFELARFYAP.
Sug1p  195  KTLLARAVAHHTDCKFIR.VSGAELVQKYIGEGSRMVRELFVMAREHAP.
ftsH   198  KTLLAKAIAGEAKVPFFT.ISGSDFVEMFVGVGASRVRDMFEQAKKAAP.
Pas1p  744  KTLLASAVAQQCGLNFIS.VKGPEILNKFIGASEQNIRELFERAQSVKP.
NSF    274  KTLLARQIGKMLNAREPKVVNGPEILNKYMGESEANIRKLFADAEEEQRR p60    328  .......STIFIDEIDSICSKR..GTGSEHEASRRVKSELLIQMDGVSGP
mei-1  287  .......SIIFIDEIDTLGGQR..GNSGEHEASRRVKSEFLVQMDG....
Sug1p  243  .......SIIFMDEIDSIGSTRVEGSGGDSEVQRTMLELLNQLDGFET.
ftsH   246  .......CIIFIDEIDAVGRQRGAGLGGGHDEREQTLNQMLVEMDGFEG.
Pas1p  792  .......CILFDEFDSIAPKRGH...DSTGVTDRVVNQLLTQMDGAEGL
NSF    324  LGANSGLHIIIFDEIDAICKQRGS.MAGSTGVHDTVVNQLLSKIDGVEQL p60    369  SAGEESSKMVMVLAATNFPWDIDEALRR..RLEKRIYIPLPEIDGREQLL
mei-1  324  SQNKFDSRRVFVLAATNIPWELDEALRR..RFEKRIFIPLPDIDARKKLI
Sug1p  285  ......SKNIKIIMATNRLDILDPAILRPGRIDRKIEFPPPSVAARAEII
ftsH   288  ......NEGIIVIAATSRPDVLDPAILRPGRFDRQVVVGLPDVRGREQII
Pas1p  832  D......GVYILAATSRPDLIDSALLRPGRLDKSVICNIPTESERLDIL
NSF    373  N......NILVIGMTNRPDLIDEAILRPGRLEVKMEIGLPDEKGRLQIL p60    417  RINL.........KEVPLADDIDLKSIAEKMDGYSGADIT
mei-1  372  EKSM.........EGTPKSDEINYDDLAARTEGFSGADVV
Sug1p  329  RIHS.........RKMNLTRGINLRKVAEKMNGCSGADVK
ftsH   332  KVHM.........RRVPLAPDIDAAIIARGTPGFSGADLA
Pas1p  875  QAIVNSKDKDTGQKKFALEKNADLKLIAEKTAGFSGADLQ
NSF    416  HI...HTARMRGHQ..LLSADVDIKELAVETKNFSGAELE
```

FIG. 1B

```
  1  MATKRAWKLQELVAHSSNVNCLALGPMSGRVMVTGGEDKK
 41  VNLWAVGKQNCIISLSGHTSPVDSVKFNSSEELVVAGSQS
 81  GTMKIYDLEPAKIVRTLTGHRNSIRCMDFHPFGEFVASGS
121  TDTNVKLWDVRRKGCIYTYKGHSDQVNMIKFSPDGKWLVT
161  ASEDTTIKLWDLTMGKLFQEFKNHTGGVTGIEFHPNEFLL
201  ASGSSDRTVQFWDLETFQLVSSTSPGASAVRSISFHPDGS
241  YLFCSSQDMLHAFGWEPIRCFDTFSVGWGKVADTVIASTQ
281  LIGASFNATNVSVYVADLSRMSTTGIAQEPQSQPSKTPSG
321  GAEEVPSKPLTASGRKNFVRERPHTTSSKQRQPDVKSEPE
361  RQSPTQDEGVKDDDATDIKDPDSYAKIFSPKTRVDHSPER
401  NAQPFPAPLDVPGAQEPEPFKHPPKPAAAAVAPVSRAPA
441  PSASDWQPAQANPAPNRVPAATKPVPAQEVAPSRKPDPIS
481  TIIPSDRNKPANLDMDAFLPPAHAQQAPRVNAPASRKQSD
521  SERIEGLRKGHDSMCQVLSSRHRNLDVVRAIWTAGDAKTS
561  VESVVNMKDQAILVDILNIMLLKKSLWNLDMCVVVLPRLK
601  ELLSSKYENYVHTSCACLKLILKNFTSLFNQNIKCPPSGI
641  DITREERYNKCSKCYSYLIATRGYVEEKQHVSGKLGSSFR
681  ELHLLLDQLE
```

FIG. 2A

```
Sp p80    4  KRAWKLQELVAHSSNVNCLALGPMSGRVMVTGGEDKKVNLWA
Hs p80    8  KTAWKLQEIVAHASNVSSLVLGKASGRLLATGGDDCRVNLWS
Hs TFIID 531 KTASELKILYGHSGPVYGASFSP.DRNYLLSSSEDGTVRLWS
Tc PkwA  489 ASGDELHTLEGHTDWVRAVAFSP.DGALLASGSDDATVRLWD

Sp p80   46  VGKQNCIISLSGHTSPVDSVKFNSSEELVVAGSQSGTMKIYD
Hs p80   50  INKPNCIMSLTGHTSPVESVRLNTPEELIVAGSQSGSIRVWD
Hs TFIID 572 LQTFTCLVGYKGHNYPVWDTQFSPYGYYFVSGGHDRVARLWA
Tc PkwA  530 VAAAEERAVFEGHTHYVLDIAFSPDGSMVASGSRDGTARLWN

Sp p80   88  LEPAKIVRTLTGHRNSIRCMDFHPFGEFVASGSTDTNVKLWD
Hs p80   92  LEAAKILRTLMGLKANICSLDFHPYGEFVASGSQDTNIKLWD
Hs TFIID 614 TDHYQFLRIFAGHLADVNCTRFHPNSNYVATGSADRTVRLWD
Tc PkwA  572 VATGTEHAVLKGHTDYVYAVAFSPDGSMVASGSRDGTIRLWD

Sp p80  130  VRRKGCIYTYKGHSDQVNMIKFSPDGKWLVTASEDTTIKLWD
Hs p80  134  IRRKGCVFRYRGHSQAVRCLRFSPDGKWLASAADDHTVKLWD
Hs TFIID 656 VLNGNCVRIFTGHKGPIHSLTFSPNGRFLATGATDGRVLLWD
Tc PkwA  614 VATGKERDVLQAPAENVVSLAFSPDGSMLVHG.SDSTVHLWD

Sp p80  172  LTMGKLFQEFKNHTGGVTGIEFHPNEFLLASGSSDRTVQFWD
Hs p80  176  LTAGKMMSEFPGHTGPVNVVEFHPNEYLLASGSSDGTIRFWD
Hs TFIID 698 IGHGLMVGELKGHTDTVCSLRFSRDGEILASGSMDNTVRLWD
Tc PkwA  655 VASGEALHTFEGHTDWVRAVAFSPDGALLASGSDDRTIRLWD

Sp p80  214  LETFQLVSSTSPGASAVRSISFHPDGSYLFCSSQDMLHAFGWE
Hs p80  218  LEKFQVVSRIECEPGPVRSVLFNPDGCCLYSGCQDSLRVYGWE
Hs TFIID 740 AIKAFEDLETDDFTTATGHINLPENSQEILLGTY..MTKSTPV
Tc PkwA  697 VAAQEEHTTLEGHTEPVHSVAFHPEGTTLASASEDGTIRIWPI
```

FIG. 2B

SEQUENCE LISTING

```
<160> NUMBER OF SEQ ID NOS: 16

<210> SEQ ID NO 1
<211> LENGTH: 516
<212> TYPE: PRT
<213> ORGANISM: Strongylocentrotus purpuratus
<220> FEATURE:
<223> OTHER INFORMATION: katanin p60 subunit

<400> SEQUENCE: 1

Met Ser Val Asp Glu Ile Cys Glu Asn Thr Lys Met Gly Arg Glu Tyr
 1               5                  10                  15

Ala Leu Leu Gly Asn Tyr Glu Thr Ser Leu Val Tyr Tyr Gln Gly Val
                20                  25                  30

Leu Gln Gln Ile Gln Lys Leu Leu Thr Ser Val His Glu Pro Gln Arg
            35                  40                  45

Lys His Gln Trp Gln Thr Ile Arg Gln Glu Leu Ser Gln Glu Tyr Glu
        50                  55                  60

His Val Lys Asn Ile Thr Lys Thr Leu Asn Gly Phe Lys Ser Glu Pro
    65                  70                  75                  80

Ala Ala Pro Glu Pro Ala Pro Asn His Arg Ala Ala Pro Phe Ser His
                85                  90                  95

His Gln His Ala Ala Lys Pro Ala Ala Ala Glu Pro Ala Arg Asp Pro
               100                 105                 110

Asp Val Trp Pro Pro Thr Pro Val Asp His Arg Pro Ser Pro Pro
           115                 120                 125

Tyr Gln Arg Ala Ala Arg Lys Asp Pro Pro Arg Arg Ser Glu Pro Ser
       130                 135                 140

Lys Pro Ala Asn Arg Ala Pro Gly Asn Asp Arg Gly Gly Arg Gly Pro
145                 150                 155                 160

Ser Asp Arg Arg Gly Asp Ala Arg Ser Gly Gly Gly Gly Arg Gly Gly
               165                 170                 175

Ala Arg Gly Ser Asp Lys Asp Lys Asn Arg Gly Gly Lys Ser Asp Lys
           180                 185                 190

Asp Lys Lys Ala Pro Ser Gly Glu Glu Gly Asp Glu Lys Lys Phe Asp
       195                 200                 205

Pro Ala Gly Tyr Asp Lys Asp Leu Val Glu Asn Leu Glu Arg Asp Ile
   210                 215                 220

Val Gln Arg Asn Pro Asn Val His Trp Ala Asp Ile Ala Gly Leu Thr
225                 230                 235                 240
```

```
Glu Ala Lys Arg Leu Leu Glu Glu Ala Val Val Leu Pro Leu Trp Met
                245                 250                 255
Pro Asp Tyr Phe Lys Gly Ile Arg Arg Pro Trp Lys Gly Val Leu Met
            260                 265                 270
Val Gly Pro Pro Gly Thr Gly Lys Thr Met Leu Ala Lys Ala Val Ala
        275                 280                 285
Thr Glu Cys Gly Thr Thr Phe Phe Asn Val Ser Ser Ala Ser Leu Thr
    290                 295                 300
Ser Lys Tyr His Gly Glu Ser Glu Lys Leu Val Arg Leu Leu Phe Glu
305                 310                 315                 320
Met Ala Arg Phe Tyr Ala Pro Ser Thr Ile Phe Ile Asp Glu Ile Asp
                325                 330                 335
Ser Ile Cys Ser Lys Arg Gly Thr Gly Ser Glu His Glu Ala Ser Arg
            340                 345                 350
Arg Val Lys Ser Glu Leu Leu Ile Gln Met Asp Gly Val Ser Gly Pro
        355                 360                 365
Ser Ala Gly Glu Glu Ser Ser Lys Met Val Met Val Leu Ala Ala Thr
    370                 375                 380
Asn Phe Pro Trp Asp Ile Asp Glu Ala Leu Arg Arg Arg Leu Glu Lys
385                 390                 395                 400
Arg Ile Tyr Ile Pro Leu Pro Glu Ile Asp Gly Arg Glu Gln Leu Leu
                405                 410                 415
Arg Ile Asn Leu Lys Glu Val Pro Leu Ala Asp Asp Ile Asp Leu Lys
            420                 425                 430
Ser Ile Ala Glu Lys Met Asp Gly Tyr Ser Gly Ala Asp Ile Thr Asn
        435                 440                 445
Val Cys Arg Asp Ala Ser Met Met Ala Met Arg Arg Arg Ile Gln Gly
    450                 455                 460
Leu Arg Pro Glu Glu Ile Arg His Ile Pro Lys Glu Glu Leu Asn Gln
465                 470                 475                 480
Pro Ser Thr Pro Ala Asp Phe Leu Leu Ala Leu Gln Lys Val Ser Lys
                485                 490                 495
Ser Val Gly Lys Glu Asp Leu Val Lys Tyr Met Ala Trp Met Glu Glu
            500                 505                 510
Phe Gly Ser Val
        515

<210> SEQ ID NO 2
<211> LENGTH: 690
<212> TYPE: PRT
<213> ORGANISM: Strongylocentrotus purpuratus
<220> FEATURE:
<223> OTHER INFORMATION: katanin p80 subunit

<400> SEQUENCE: 2

Met Ala Thr Lys Arg Ala Trp Lys Leu Gln Glu Leu Val Ala His Ser
1               5                   10                  15
Ser Asn Val Asn Cys Leu Ala Leu Gly Pro Met Ser Gly Arg Val Met
                20                  25                  30
Val Thr Gly Gly Glu Asp Lys Lys Val Asn Leu Trp Ala Val Gly Lys
            35                  40                  45
Gln Asn Cys Ile Ile Ser Leu Ser Gly His Thr Ser Pro Val Asp Ser
        50                  55                  60
Val Lys Phe Asn Ser Ser Glu Glu Leu Val Val Ala Gly Ser Gln Ser
65                  70                  75                  80
```

-continued

```
Gly Thr Met Lys Ile Tyr Asp Leu Glu Pro Ala Lys Ile Val Arg Thr
                 85                  90                  95
Leu Thr Gly His Arg Asn Ser Ile Arg Cys Met Asp Phe His Pro Phe
            100                 105                 110
Gly Glu Phe Val Ala Ser Gly Ser Thr Asp Thr Asn Val Lys Leu Trp
        115                 120                 125
Asp Val Arg Arg Lys Gly Cys Ile Tyr Thr Tyr Lys Gly His Ser Asp
    130                 135                 140
Gln Val Asn Met Ile Lys Phe Ser Pro Asp Gly Lys Trp Leu Val Thr
145                 150                 155                 160
Ala Ser Glu Asp Thr Thr Ile Lys Leu Trp Asp Leu Thr Met Gly Lys
                165                 170                 175
Leu Phe Gln Glu Phe Lys Asn His Thr Gly Gly Val Thr Gly Ile Glu
            180                 185                 190
Phe His Pro Asn Glu Phe Leu Leu Ala Ser Gly Ser Ser Asp Arg Thr
        195                 200                 205
Val Gln Phe Trp Asp Leu Glu Thr Phe Gln Leu Val Ser Ser Thr Ser
    210                 215                 220
Pro Gly Ala Ser Ala Val Arg Ser Ile Ser Phe His Pro Asp Gly Ser
225                 230                 235                 240
Tyr Leu Phe Cys Ser Ser Gln Asp Met Leu His Ala Phe Gly Trp Glu
                245                 250                 255
Pro Ile Arg Cys Phe Asp Thr Phe Ser Val Gly Trp Gly Lys Val Ala
            260                 265                 270
Asp Thr Val Ile Ala Ser Thr Gln Leu Ile Gly Ala Ser Phe Asn Ala
        275                 280                 285
Thr Asn Val Ser Val Tyr Val Ala Asp Leu Ser Arg Met Ser Thr Thr
    290                 295                 300
Gly Ile Ala Gln Glu Pro Gln Ser Gln Pro Ser Lys Thr Pro Ser Gly
305                 310                 315                 320
Gly Ala Glu Glu Val Pro Ser Lys Pro Leu Thr Ala Ser Gly Arg Lys
                325                 330                 335
Asn Phe Val Arg Glu Arg Pro His Thr Thr Ser Ser Lys Gln Arg Gln
            340                 345                 350
Pro Asp Val Lys Ser Glu Pro Glu Arg Gln Ser Pro Thr Gln Asp Glu
        355                 360                 365
Gly Val Lys Asp Asp Asp Ala Thr Asp Ile Lys Asp Pro Asp Ser Tyr
    370                 375                 380
Ala Lys Ile Phe Ser Pro Lys Thr Arg Val Asp His Ser Pro Glu Arg
385                 390                 395                 400
Asn Ala Gln Pro Phe Pro Ala Pro Leu Asp Val Pro Gly Ala Gln Glu
                405                 410                 415
Pro Glu Pro Phe Lys His Pro Pro Lys Pro Ala Ala Ala Ala Ala Val
            420                 425                 430
Ala Pro Val Ser Arg Ala Pro Ala Pro Ser Ala Ser Asp Trp Gln Pro
        435                 440                 445
Ala Gln Ala Asn Pro Ala Pro Asn Arg Val Pro Ala Ala Thr Lys Pro
    450                 455                 460
Val Pro Ala Gln Glu Val Ala Pro Ser Arg Lys Pro Asp Pro Ile Ser
465                 470                 475                 480
Thr Ile Ile Pro Ser Asp Arg Asn Lys Pro Ala Asn Leu Asp Met Asp
                485                 490                 495
```

```
Ala Phe Leu Pro Pro Ala His Ala Gln Gln Ala Pro Arg Val Asn Ala
                500                 505                 510

Pro Ala Ser Arg Lys Gln Ser Asp Ser Glu Arg Ile Glu Gly Leu Arg
            515                 520                 525

Lys Gly His Asp Ser Met Cys Gln Val Leu Ser Ser Arg His Arg Asn
        530                 535                 540

Leu Asp Val Val Arg Ala Ile Trp Thr Ala Gly Asp Ala Lys Thr Ser
545                 550                 555                 560

Val Glu Ser Val Val Asn Met Lys Asp Gln Ala Ile Leu Val Asp Ile
                565                 570                 575

Leu Asn Ile Met Leu Leu Lys Lys Ser Leu Trp Asn Leu Asp Met Cys
            580                 585                 590

Val Val Val Leu Pro Arg Leu Lys Glu Leu Leu Ser Ser Lys Tyr Glu
            595                 600                 605

Asn Tyr Val His Thr Ser Cys Ala Cys Leu Lys Leu Ile Leu Lys Asn
        610                 615                 620

Phe Thr Ser Leu Phe Asn Gln Asn Ile Lys Cys Pro Pro Ser Gly Ile
625                 630                 635                 640

Asp Ile Thr Arg Glu Glu Arg Tyr Asn Lys Cys Ser Lys Cys Tyr Ser
                645                 650                 655

Tyr Leu Ile Ala Thr Arg Gly Tyr Val Glu Glu Lys Gln His Val Ser
            660                 665                 670

Gly Lys Leu Gly Ser Ser Phe Arg Glu Leu His Leu Leu Leu Asp Gln
        675                 680                 685

Leu Glu
    690

<210> SEQ ID NO 3
<211> LENGTH: 730
<212> TYPE: PRT
<213> ORGANISM: Xenopus laevis
<220> FEATURE:
<223> OTHER INFORMATION: Xenopus kinesin central motor 1 (XKCM1)

<400> SEQUENCE: 3

Met Glu Arg Leu Val Ala Thr Arg Leu Val Thr Gly Leu Ala Val Lys
 1               5                  10                  15

Ile Met Arg Ser Asn Gly Val Ile His Asn Ala Asn Ile Thr Ser Val
                20                  25                  30

Asn Met Asp Arg Ser Ser Val Asn Val Glu Trp Lys Glu Gly Glu Ala
            35                  40                  45

Asn Lys Gly Lys Glu Ile Ser Phe Ala Asp Val Ile Ser Val Asn Pro
        50                  55                  60

Glu Leu Leu Asp Ala Val Leu Ala Pro Thr Asn Val Lys Glu Asn Met
65                  70                  75                  80

Pro Pro Gln Arg Asn Val Ser Ser Gln Asn His Lys Arg Lys Thr Ile
                85                  90                  95

Ser Lys Ile Pro Ala Pro Lys Val Ala Ala Lys Asn Ser Leu Leu
            100                 105                 110

Ser Glu Ser Gly Ala Gln Ser Val Leu Arg Glu Arg Ser Thr Arg Met
        115                 120                 125

Thr Ala Ile His Glu Thr Leu Pro Tyr Glu Asn Glu Met Glu Ala Glu
    130                 135                 140

Ser Thr Pro Leu Pro Ile Gln Gln Asn Ser Val Gln Ala Arg Ser Arg
145                 150                 155                 160
```

-continued

```
Ser Thr Lys Val Ser Ile Ala Glu Glu Pro Arg Leu Gln Thr Arg Ile
            165                 170                 175
Ser Glu Ile Val Glu Glu Ser Leu Pro Ser Gly Arg Asn Asn Gln Gly
            180                 185                 190
Arg Arg Lys Ser Asn Ile Val Lys Glu Met Glu Lys Met Lys Asn Lys
            195                 200                 205
Arg Glu Glu Gln Arg Ala Gln Asn Tyr Glu Arg Met Lys Arg Ala
210                 215                 220
Gln Asp Tyr Asp Thr Ser Val Pro Asn Trp Glu Phe Gly Lys Met Ile
225                 230                 235                 240
Lys Glu Phe Arg Ala Thr Met Asp Cys His Arg Ile Ser Met Ala Asp
                245                 250                 255
Pro Ala Glu Glu His Arg Ile Cys Val Cys Val Arg Lys Arg Pro Leu
            260                 265                 270
Asn Lys Gln Glu Leu Ser Lys Lys Glu Ile Asp Ile Ser Val Pro
            275                 280                 285
Ser Lys Asn Ile Val Leu Val His Glu Pro Lys Leu Lys Val Asp Leu
            290                 295                 300
Thr Lys Tyr Leu Glu Asn Gln Ala Phe Arg Phe Asp Phe Ser Phe Asp
305                 310                 315                 320
Glu Thr Ala Thr Asn Glu Val Val Tyr Arg Phe Thr Ala Arg Pro Leu
                325                 330                 335
Val Gln Ser Ile Phe Glu Gly Gly Lys Ala Thr Cys Phe Ala Tyr Gly
            340                 345                 350
Gln Thr Gly Ser Gly Lys Thr His Thr Met Gly Gly Asp Phe Ser Gly
            355                 360                 365
Lys Ser Gln Asn Val Ser Lys Gly Val Tyr Ala Phe Ala Ser Arg Asp
            370                 375                 380
Val Phe Leu Leu Leu Asp Gln Pro Arg Tyr Lys His Leu Asp Leu Asp
385                 390                 395                 400
Val Phe Val Thr Phe Phe Glu Ile Tyr Asn Gly Lys Val Phe Asp Leu
                405                 410                 415
Leu Asn Lys Lys Thr Lys Leu Arg Val Leu Glu Asp Ala Lys Gln Glu
            420                 425                 430
Val Gln Val Val Gly Leu Leu Glu Lys Gln Val Ile Ser Ala Asp Asp
            435                 440                 445
Val Phe Lys Met Ile Glu Ile Gly Ser Ala Cys Arg Thr Ser Gly Gln
            450                 455                 460
Thr Phe Ala Asn Thr Ser Ser Arg Ser His Ala Cys Leu Gln Ile
465                 470                 475                 480
Ile Leu Arg Arg Gly Ser Lys Leu His Gly Lys Phe Ser Leu Val Asp
                485                 490                 495
Leu Ala Gly Asn Glu Arg Gly Val Asp Thr Ala Ser Ala Asp Arg Ile
            500                 505                 510
Thr Arg Met Lys Gly Ala Glu Ile Asn Arg Ser Leu Leu Ala Leu Lys
            515                 520                 525
Glu Cys Ile Arg Ala Leu Gly Gln Asn Lys Ser His Thr Pro Phe Arg
            530                 535                 540
Glu Ser Lys Leu Thr Gln Ile Leu Arg Asp Ser Phe Ile Gly Glu Asn
545                 550                 555                 560
Ser Arg Thr Cys Met Ile Ala Met Leu Ser Pro Gly Phe Asn Ser Cys
                565                 570                 575
Glu Tyr Thr Leu Asn Thr Leu Arg Tyr Ala Asp Arg Val Lys Glu Leu
```

-continued

```
                  580                 585                 590
Ser Pro Gln Asn Ala Glu Thr Asn Asp Asp Asn Leu Gln Met Glu Asp
        595                 600                 605

Ser Gly Gly Ser His Ala Ser Ile Glu Gly Leu Gln Leu Gln Asp Asp
    610                 615                 620

Phe Leu Leu Lys Asp Glu Glu Leu Ser Thr His Asn Ser Phe Gln Asp
625                 630                 635                 640

Ala Leu Asn Arg Val Gly Glu Leu Glu Asp Lys Ala Val Asp Glu Leu
                645                 650                 655

Arg Glu Leu Val Gln Lys Glu Pro Glu Trp Thr Asn Leu Leu Gln Met
                660                 665                 670

Thr Glu Gln Pro Asp Tyr Asp Leu Glu Asn Phe Val Met Gln Ala Glu
            675                 680                 685

Tyr Leu Ile Gln Glu Arg Ser Lys Val Leu Ile Ala Leu Gly Asp Ser
    690                 695                 700

Ile Asn Ser Leu Arg Leu Ala Leu Gln Val Glu Gln Ala Ser Lys
705                 710                 715                 720

Gln Ile Ser Lys Lys Arg Ser Asn Lys
                725                 730

<210> SEQ ID NO 4
<211> LENGTH: 217
<212> TYPE: PRT
<213> ORGANISM: Strongylocentrotus purpuratus
<220> FEATURE:
<223> OTHER INFORMATION: AAA ATPase superfamily katanin p60 AAA domain

<400> SEQUENCE: 4

Val His Trp Ala Asp Ile Ala Gly Leu Thr Glu Ala Lys Arg Leu Leu
  1               5                  10                  15

Glu Glu Ala Val Val Leu Pro Leu Trp Met Pro Asp Tyr Phe Lys Gly
            20                  25                  30

Ile Arg Arg Pro Trp Lys Gly Val Leu Met Val Gly Pro Pro Gly Thr
        35                  40                  45

Gly Lys Thr Met Leu Ala Lys Ala Val Ala Thr Glu Cys Gly Thr Thr
    50                  55                  60

Phe Phe Asn Val Ser Ser Ala Ser Leu Thr Ser Lys Tyr His Gly Glu
65                  70                  75                  80

Ser Glu Lys Leu Val Arg Leu Leu Phe Glu Met Ala Arg Phe Tyr Ala
                85                  90                  95

Pro Ser Thr Ile Phe Ile Asp Glu Ile Asp Ser Ile Cys Ser Lys Arg
            100                 105                 110

Gly Thr Gly Ser Glu His Glu Ala Ser Arg Arg Val Lys Ser Glu Leu
        115                 120                 125

Leu Ile Gln Met Asp Gly Val Ser Gly Pro Ser Ala Gly Glu Glu Ser
    130                 135                 140

Ser Lys Met Val Met Val Leu Ala Ala Thr Asn Phe Pro Trp Asp Ile
145                 150                 155                 160

Asp Glu Ala Leu Arg Arg Arg Leu Glu Lys Arg Ile Tyr Ile Pro Leu
                165                 170                 175

Pro Glu Ile Asp Gly Arg Glu Gln Leu Leu Arg Ile Asn Leu Lys Glu
            180                 185                 190

Val Pro Leu Ala Asp Asp Ile Asp Leu Lys Ser Ile Ala Glu Lys Met
        195                 200                 205

Asp Gly Tyr Ser Gly Ala Asp Ile Thr
```

210               215

<210> SEQ ID NO 5
<211> LENGTH: 213
<212> TYPE: PRT
<213> ORGANISM: Caenorhabditis elegans
<220> FEATURE:
<223> OTHER INFORMATION: AAA ATPase superfamily mei-1 AAA domain

<400> SEQUENCE: 5

Met Ser Leu Asp Asp Ile Ile Gly Met His Asp Val Lys Gln Val Leu
 1               5                  10                  15

His Glu Ala Val Thr Leu Pro Leu Val Pro Glu Phe Phe Gln Gly
            20                  25                  30

Leu Arg Ser Pro Trp Lys Ala Met Val Leu Ala Gly Pro Gly Thr
        35                  40                  45

Gly Lys Thr Leu Ile Ala Arg Ala Ile Ala Ser Glu Ser Ser Ser Thr
    50                  55                  60

Phe Phe Thr Val Ser Ser Thr Asp Leu Ser Ser Lys Trp Arg Gly Asp
65                  70                  75                  80

Ser Glu Lys Ile Val Arg Leu Leu Phe Glu Leu Ala Arg Phe Tyr Ala
                85                  90                  95

Pro Ser Ile Ile Phe Ile Asp Glu Ile Asp Thr Leu Gly Gly Gln Arg
            100                 105                 110

Gly Asn Ser Gly Glu His Glu Ala Ser Arg Arg Val Lys Ser Glu Phe
        115                 120                 125

Leu Val Gln Met Asp Gly Ser Gln Asn Lys Phe Asp Ser Arg Arg Val
    130                 135                 140

Phe Val Leu Ala Ala Thr Asn Ile Pro Trp Glu Leu Asp Glu Ala Leu
145                 150                 155                 160

Arg Arg Arg Phe Glu Lys Arg Ile Phe Ile Pro Leu Pro Asp Ile Asp
                165                 170                 175

Ala Arg Lys Lys Leu Ile Glu Lys Ser Met Glu Gly Thr Pro Lys Ser
            180                 185                 190

Asp Glu Ile Asn Tyr Asp Asp Leu Ala Ala Arg Thr Glu Gly Phe Ser
        195                 200                 205

Gly Ala Asp Val Val
    210

<210> SEQ ID NO 6
<211> LENGTH: 215
<212> TYPE: PRT
<213> ORGANISM: Saccharomyces cerevisiae
<220> FEATURE:
<223> OTHER INFORMATION: AAA ATPase superfamily sug1 AAA domain

<400> SEQUENCE: 6

Ser Thr Tyr Asp Met Val Gly Gly Leu Thr Lys Gln Ile Lys Glu Ile
 1               5                  10                  15

Lys Glu Val Ile Glu Leu Pro Val Lys His Pro Glu Leu Phe Glu Ser
            20                  25                  30

Leu Gly Ile Ala Gln Pro Lys Gly Val Ile Leu Tyr Gly Pro Pro Gly
        35                  40                  45

Thr Gly Lys Thr Leu Leu Ala Arg Ala Val Ala His His Thr Asp Cys
    50                  55                  60

Lys Phe Ile Arg Val Ser Gly Ala Glu Leu Val Gln Lys Tyr Ile Gly
65                  70                  75                  80

```
Glu Gly Ser Arg Met Val Arg Glu Leu Phe Val Met Ala Arg Glu His
                85                  90                  95

Ala Pro Ser Ile Ile Phe Met Asp Glu Ile Asp Ser Ile Gly Ser Thr
                100                 105                 110

Arg Val Glu Gly Ser Gly Gly Asp Ser Glu Val Gln Arg Thr Met
                115                 120                 125

Leu Glu Leu Leu Asn Gln Leu Asp Gly Phe Glu Thr Ser Lys Asn Ile
    130                 135                 140

Lys Ile Ile Met Ala Thr Asn Arg Leu Asp Ile Leu Asp Pro Ala Leu
145                 150                 155                 160

Leu Arg Pro Gly Arg Ile Asp Arg Lys Ile Glu Phe Pro Pro Ser
                165                 170                 175

Val Ala Ala Arg Ala Glu Ile Leu Arg Ile His Ser Arg Lys Met Asn
                180                 185                 190

Leu Thr Arg Gly Ile Asn Leu Arg Lys Val Ala Glu Lys Met Asn Gly
                195                 200                 205

Cys Ser Gly Ala Asp Val Lys
    210                 215

<210> SEQ ID NO 7
<211> LENGTH: 214
<212> TYPE: PRT
<213> ORGANISM: Escherichia coli
<220> FEATURE:
<223> OTHER INFORMATION: AAA ATPase superfamily ftsH AAA domain

<400> SEQUENCE: 7

Thr Thr Phe Ala Asp Val Ala Gly Cys Asp Glu Ala Lys Glu Glu Val
  1                 5                  10                  15

Ala Glu Leu Val Glu Tyr Leu Arg Glu Pro Ser Arg Phe Gln Lys Leu
                20                  25                  30

Gly Gly Lys Ile Pro Lys Gly Val Leu Met Val Gly Pro Pro Gly Thr
            35                  40                  45

Gly Lys Thr Leu Leu Ala Lys Ala Ile Ala Gly Glu Ala Lys Val Pro
    50                  55                  60

Phe Phe Thr Ile Ser Gly Ser Asp Phe Val Glu Met Phe Val Gly Val
 65                 70                  75                  80

Gly Ala Ser Arg Val Arg Asp Met Phe Glu Gln Ala Lys Lys Ala Ala
                85                  90                  95

Pro Cys Ile Ile Phe Ile Asp Glu Ile Asp Ala Val Gly Arg Gln Arg
                100                 105                 110

Gly Ala Gly Leu Gly Gly Gly His Asp Glu Arg Glu Gln Thr Leu Asn
            115                 120                 125

Gln Met Leu Val Glu Met Asp Gly Phe Glu Gly Asn Glu Gly Ile Ile
    130                 135                 140

Val Ile Ala Ala Thr Asn Arg Pro Asp Val Leu Asp Pro Ala Leu Leu
145                 150                 155                 160

Arg Pro Gly Arg Phe Asp Arg Gln Val Val Gly Leu Pro Asp Val
                165                 170                 175

Arg Gly Arg Glu Gln Ile Leu Lys Val His Met Arg Arg Val Pro Leu
                180                 185                 190

Ala Pro Asp Ile Asp Ala Ala Ile Ile Ala Arg Gly Thr Pro Gly Phe
                195                 200                 205

Ser Gly Ala Asp Leu Ala
    210
```

```
<210> SEQ ID NO 8
<211> LENGTH: 221
<212> TYPE: PRT
<213> ORGANISM: Saccharomyces cerevisiae
<220> FEATURE:
<223> OTHER INFORMATION: AAA ATPase superfamily PAS1 AAA domain

<400> SEQUENCE: 8

Ile Lys Trp Gly Asp Ile Gly Ala Leu Ala Asn Ala Lys Asp Val Leu
 1               5                  10                  15

Leu Glu Thr Leu Glu Trp Pro Thr Lys Tyr Glu Pro Ile Phe Val Asn
            20                  25                  30

Cys Pro Leu Arg Leu Arg Ser Gly Ile Leu Leu Tyr Gly Tyr Pro Gly
        35                  40                  45

Cys Gly Lys Thr Leu Leu Ala Ser Ala Val Ala Gln Gln Cys Gly Leu
    50                  55                  60

Asn Phe Ile Ser Val Lys Gly Pro Glu Ile Leu Asn Lys Phe Ile Gly
65                  70                  75                  80

Ala Ser Glu Gln Asn Ile Arg Glu Leu Phe Glu Arg Ala Gln Ser Val
                85                  90                  95

Lys Pro Cys Ile Leu Phe Phe Asp Glu Phe Asp Ser Ile Ala Pro Lys
            100                 105                 110

Arg Gly His Asp Ser Thr Gly Val Thr Asp Arg Val Val Asn Gln Leu
        115                 120                 125

Leu Thr Gln Met Asp Gly Ala Glu Gly Leu Asp Gly Val Tyr Ile Leu
    130                 135                 140

Ala Ala Thr Ser Arg Pro Asp Leu Ile Asp Ser Ala Leu Leu Arg Pro
145                 150                 155                 160

Gly Arg Leu Asp Lys Ser Val Ile Cys Asn Ile Pro Thr Glu Ser Glu
                165                 170                 175

Arg Leu Asp Ile Leu Gln Ala Ile Val Asn Ser Lys Asp Lys Asp Thr
            180                 185                 190

Gly Gln Lys Lys Phe Ala Leu Gly Lys Asn Ala Asp Leu Lys Leu Ile
        195                 200                 205

Ala Glu Lys Thr Ala Gly Phe Ser Gly Ala Asp Leu Gln
    210                 215                 220

<210> SEQ ID NO 9
<211> LENGTH: 227
<212> TYPE: PRT
<213> ORGANISM: Cricetulus longicaudatus
<220> FEATURE:
<223> OTHER INFORMATION: AAA ATPase superfamily N-ethylmaleimide
      sensitive fusion protein (NSF) AAA domain

<400> SEQUENCE: 9

Glu Lys Met Gly Ile Gly Gly Leu Asp Lys Glu Phe Ser Asp Ile Phe
 1               5                  10                  15

Arg Arg Ala Phe Ala Ser Arg Val Phe Pro Pro Glu Ile Val Glu Gln
            20                  25                  30

Met Gly Cys Lys His Val Lys Gly Ile Leu Leu Tyr Gly Pro Pro Gly
        35                  40                  45

Cys Gly Lys Thr Leu Leu Ala Arg Gln Ile Gly Lys Met Leu Asn Ala
    50                  55                  60

Arg Glu Pro Lys Val Val Asn Gly Pro Glu Ile Leu Asn Lys Tyr Val
65                  70                  75                  80

Gly Glu Ser Glu Ala Asn Ile Arg Lys Leu Phe Ala Asp Ala Glu Glu
```

```
                        85                  90                  95
Glu Gln Arg Arg Leu Gly Ala Asn Ser Gly Leu His Ile Ile Ile Phe
                100                 105                 110

Asp Glu Ile Asp Ala Ile Cys Lys Gln Arg Gly Ser Met Ala Gly Ser
                115                 120                 125

Thr Gly Val His Asp Thr Val Val Asn Gln Leu Leu Ser Lys Ile Asp
            130                 135                 140

Gly Val Glu Gln Leu Asn Asn Ile Leu Val Ile Gly Met Thr Asn Arg
145                 150                 155                 160

Pro Asp Leu Ile Asp Glu Ala Leu Leu Arg Pro Gly Arg Leu Glu Val
                165                 170                 175

Lys Met Glu Ile Gly Leu Pro Asp Glu Lys Gly Arg Leu Gln Ile Leu
                180                 185                 190

His Ile His Thr Ala Arg Met Arg Gly His Gln Leu Leu Ser Ala Asp
            195                 200                 205

Val Asp Ile Lys Glu Leu Ala Val Glu Thr Lys Asn Phe Ser Gly Ala
        210                 215                 220

Glu Leu Glu
225

<210> SEQ ID NO 10
<211> LENGTH: 253
<212> TYPE: PRT
<213> ORGANISM: Strongylocentrotus purpuratus
<220> FEATURE:
<223> OTHER INFORMATION: katanin p80 subunit WD40 repeat region

<400> SEQUENCE: 10

Lys Arg Ala Trp Lys Leu Gln Glu Leu Val Ala His Ser Ser Asn Val
  1               5                  10                  15

Asn Cys Leu Ala Leu Gly Pro Met Ser Gly Arg Val Met Val Thr Gly
                 20                  25                  30

Gly Glu Asp Lys Lys Val Asn Leu Trp Ala Val Gly Lys Gln Asn Cys
             35                  40                  45

Ile Ile Ser Leu Ser Gly His Thr Ser Pro Val Asp Ser Val Lys Phe
         50                  55                  60

Asn Ser Ser Glu Glu Leu Val Val Ala Gly Ser Gln Ser Gly Thr Met
 65                  70                  75                  80

Lys Ile Tyr Asp Leu Glu Pro Ala Lys Ile Val Arg Thr Leu Thr Gly
                 85                  90                  95

His Arg Asn Ser Ile Arg Cys Met Asp Phe His Pro Phe Gly Glu Phe
                100                 105                 110

Val Ala Ser Gly Ser Thr Asp Thr Asn Val Lys Leu Trp Asp Val Arg
            115                 120                 125

Arg Lys Gly Cys Ile Tyr Thr Tyr Lys Gly His Ser Asp Gln Val Asn
        130                 135                 140

Met Ile Lys Phe Ser Pro Asp Gly Lys Trp Leu Val Thr Ala Ser Glu
145                 150                 155                 160

Asp Thr Thr Ile Lys Leu Trp Asp Leu Thr Met Gly Lys Leu Phe Gln
                165                 170                 175

Glu Phe Lys Asn His Thr Gly Gly Val Thr Gly Ile Glu Phe His Pro
                180                 185                 190

Asn Glu Phe Leu Leu Ala Ser Gly Ser Ser Asp Arg Thr Val Gln Phe
            195                 200                 205

Trp Asp Leu Glu Thr Phe Gln Leu Val Ser Ser Thr Ser Pro Gly Ala
```

```
                210            215                220
Ser Ala Val Arg Ser Ile Ser Phe His Pro Asp Gly Ser Tyr Leu Phe
225                 230                235                240

Cys Ser Ser Gln Asp Met Leu His Ala Phe Gly Trp Glu
                245                250

<210> SEQ ID NO 11
<211> LENGTH: 210
<212> TYPE: PRT
<213> ORGANISM: Homo sapiens
<220> FEATURE:
<223> OTHER INFORMATION: putative human ortholog of katanin p80 (Hs p80)
      WD40 repeat region

<400> SEQUENCE: 11

Lys Thr Ala Trp Lys Leu Gln Glu Ile Val Ala His Ala Ser Asn Val
  1               5                  10                 15

Ser Ser Leu Val Leu Gly Lys Ala Ser Gly Arg Leu Leu Ala Thr Gly
                 20                  25                 30

Gly Asp Asp Cys Arg Val Asn Leu Trp Ser Ile Asn Lys Pro Asn Cys
             35                  40                 45

Ile Met Ser Leu Thr Gly His Thr Ser Pro Val Glu Ser Val Arg Leu
         50                  55                 60

Asn Thr Pro Glu Glu Leu Ile Val Ala Gly Ser Gln Ser Gly Ser Ile
 65                  70                  75                 80

Arg Val Trp Asp Leu Glu Ala Ala Lys Ile Leu Arg Thr Leu Met Gly
                 85                  90                 95

Leu Lys Ala Asn Ile Cys Ser Leu Asp Phe His Pro Tyr Gly Glu Phe
                100                 105                110

Val Ala Ser Gly Ser Gln Asp Thr Asn Ile Lys Leu Trp Asp Ile Arg
            115                 120                 125

Arg Lys Gly Cys Val Phe Arg Tyr Arg Gly His Ser Gln Ala Val Arg
        130                 135                 140

Cys Leu Arg Phe Ser Pro Asp Gly Lys Trp Leu Ala Ser Ala Ala Asp
145                 150                 155                160

Asp His Thr Val Lys Leu Trp Asp Leu Thr Ala Gly Lys Met Met Ser
                165                 170                 175

Glu Phe Pro Gly His Thr Gly Pro Val Asn Val Val Glu Phe His Pro
            180                 185                 190

Asn Glu Tyr Leu Leu Ala Ser Gly Ser Ser Asp Gly Thr Ile Arg Phe
        195                 200                 205

Trp Asp
210

<210> SEQ ID NO 12
<211> LENGTH: 250
<212> TYPE: PRT
<213> ORGANISM: Homo sapiens
<220> FEATURE:
<223> OTHER INFORMATION: TFIID WD40 repeat region

<400> SEQUENCE: 12

Lys Thr Ala Ser Glu Leu Lys Ile Leu Tyr Gly His Ser Gly Pro Val
  1               5                  10                 15

Tyr Gly Ala Ser Phe Ser Pro Asp Arg Asn Tyr Leu Leu Ser Ser Ser
                 20                  25                 30

Glu Asp Gly Thr Val Arg Leu Trp Ser Leu Gln Thr Phe Thr Cys Leu
             35                  40                 45
```

```
Val Gly Tyr Lys Gly His Asn Tyr Pro Val Trp Asp Thr Gln Phe Ser
     50                  55                  60

Pro Tyr Gly Tyr Phe Val Ser Gly His Asp Arg Val Ala Arg
65                  70                  75                  80

Leu Trp Ala Thr Asp His Tyr Gln Pro Leu Arg Ile Phe Ala Gly His
                85                  90                  95

Leu Ala Asp Val Asn Cys Thr Arg Phe His Pro Asn Ser Asn Tyr Val
                100                 105                 110

Ala Thr Gly Ser Ala Asp Arg Thr Val Arg Leu Trp Asp Val Leu Asn
                115                 120                 125

Gly Asn Cys Val Arg Ile Phe Thr Gly His Lys Gly Pro Ile His Ser
130                 135                 140

Leu Thr Phe Ser Pro Asn Gly Arg Phe Leu Ala Thr Gly Ala Thr Asp
145                 150                 155                 160

Gly Arg Val Leu Leu Trp Asp Ile Gly His Gly Leu Met Val Gly Glu
                165                 170                 175

Leu Lys Gly His Thr Asp Thr Val Cys Ser Leu Arg Phe Ser Arg Asp
                180                 185                 190

Gly Glu Ile Leu Ala Ser Gly Ser Met Asp Asn Thr Val Arg Leu Trp
                195                 200                 205

Asp Ala Ile Lys Ala Phe Glu Asp Leu Glu Thr Asp Asp Phe Thr Thr
210                 215                 220

Ala Thr Gly His Ile Asn Leu Pro Glu Asn Ser Gln Glu Leu Leu Leu
225                 230                 235                 240

Gly Thr Tyr Met Thr Lys Ser Thr Pro Val
                245                 250

<210> SEQ ID NO 13
<211> LENGTH: 251
<212> TYPE: PRT
<213> ORGANISM: Thermomonospora curvata
<220> FEATURE:
<223> OTHER INFORMATION: putative serine/threonine kinase PkwA WD40
      repeat region

<400> SEQUENCE: 13

Ala Ser Gly Asp Glu Leu His Thr Leu Glu Gly His Thr Asp Trp Val
1               5                   10                  15

Arg Ala Val Ala Phe Ser Pro Asp Gly Ala Leu Leu Ala Ser Gly Ser
                20                  25                  30

Asp Asp Ala Thr Val Arg Leu Trp Asp Val Ala Ala Glu Glu Arg
            35                  40                  45

Ala Val Phe Glu Gly His Thr His Tyr Val Leu Asp Ile Ala Phe Ser
    50                  55                  60

Pro Asp Gly Ser Met Val Ala Ser Gly Ser Arg Asp Gly Thr Ala Arg
65                  70                  75                  80

Leu Trp Asn Val Ala Thr Gly Thr Glu His Ala Val Leu Lys Gly His
                85                  90                  95

Thr Asp Tyr Val Tyr Ala Val Ala Phe Ser Pro Asp Gly Ser Met Val
                100                 105                 110

Ala Ser Gly Ser Arg Asp Gly Thr Ile Arg Leu Trp Asp Val Ala Thr
                115                 120                 125

Gly Lys Glu Arg Asp Val Leu Gln Ala Pro Ala Glu Asn Val Val Ser
130                 135                 140

Leu Ala Phe Ser Pro Asp Gly Ser Met Leu Val His Gly Ser Asp Ser
```

-continued

```
145                 150                 155                 160
Thr Val His Leu Trp Asp Val Ala Ser Gly Glu Ala Leu His Thr Phe
            165                 170                 175

Glu Gly His Thr Asp Trp Val Arg Ala Val Ala Phe Ser Pro Asp Gly
            180                 185                 190

Ala Leu Leu Ala Ser Gly Ser Asp Asp Arg Thr Ile Arg Leu Trp Asp
            195                 200                 205

Val Ala Ala Gln Glu Glu His Thr Thr Leu Glu Gly His Thr Glu Pro
        210                 215                 220

Val His Ser Val Ala Phe His Pro Glu Gly Thr Thr Leu Ala Ser Ala
225                 230                 235                 240

Ser Glu Asp Gly Thr Ile Arg Ile Trp Pro Ile
                245                 250

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:(His)6 or
      6xHis tag

<400> SEQUENCE: 14

His His His His His His
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:katanin p80
      peptide

<400> SEQUENCE: 15

Asp Ala Ser Met Met Ala Met
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:katanin p80
      peptide

<400> SEQUENCE: 16

Ile Gln Gly Leu Arg
  1               5
```

POLYPEPTIDES FOR THE DETECTION OF MICROTUBULE DEPOLYMERIZATION INHIBITORS

CROSS-REFERENCE TO RELATED APPLICATIONS

This application claims benefit under 35 U.S.C. § 119(e) of provisional patent U.S. S No. 60/081,734, filed on Apr. 14, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates assay for agents that modulate (e.g. upregulate, downregulate or completely inhibit) microtubule depolymerizing or microtubule severing proteins. Such agents will have profound effects on progression of the cell cycle and act as potent anti-mitotic agents.

BACKGROUND OF THE INVENTION

The cytoskeleton constitutes a large family of proteins that are involved in many critical processes of biology, such as chromosome and cell division, cell motility and intracellular transport (Vale and Kreis, (1993) *Guidebook to the Cytoskeletal and Motor Proteins* New York: Oxford University Press; Alberts et al., (1994) *Molecular Biology of the Cell*, 788–858). Cytoskeletal proteins are found in all cells and are involved in the pathogenesis of a large range of clinical diseases. The cytoskeleton includes a collection of polymer proteins, microtubules, actin, intermediate filaments, and septins, as well as a wide variety of proteins that bind to these polymers (polymer-interacting proteins). Some of the polymer-interacting proteins are molecular motors (myosins, kinesins, dyneins) (Goldstein (1993) *Ann. Rev. Genetics* 27: 319–351; Mooseker and Cheney (1995) *Annu. Rev. Cell Biol.* 11: 633–675) that are essential for transporting material within cells (e.g., chromosomal movement during metaphase), for muscle contraction, and for cell migration. Other groups of proteins (e.g., vinculin, talin and alpha-actinin) link different filaments, connect the cytoskeleton to the plasma membrane, control the assembly and disassembly of the cytoskeletal polymers, and moderate the organization of the polymers within cells.

Given the central role of the cytoskeleton in cell division, cell migration, inflammation, and fungal/parasitic life cycles, it is a fertile system for drug discovery. Although much is known about the molecular and structural properties of cytoskeletal components, relatively little is known about how to efficiently manipulate cytoskeletal structure and function. Such manipulation requires the discovery and development of specific compounds that can predictably and safely alter cytoskeletal structure and function. However, at present, drug targets in the cytoskeleton have been relatively untapped. Extensive work has been directed towards drugs that interact with the cytoskeletal polymers themselves (e.g., taxol and vincristine), and towards motility assays (Turner et al. (1996) *Anal. Biochem.* 242 (1): 20–5; Gittes et al. (1996) *Biophys. J* 70 (1): 418–29; Shirakawa et al. (1995) *J. Exp. Biol.* 198: 1809–15; Winkelmann et al. (1995) *Biophys. J.* 68: 2444–53; and Winkelmann et al. (1995) *Biophys. J* 68: 72S). Virtually no effort has been directed to finding drugs that target the cytoskeletal proteins that bind to the different filaments, which might be more specific targets with fewer unwanted side effects.

SUMMARY OF THE INVENTION

This invention pertains to the discovery that proteins (e.g. motor proteins) that either depolymerize or sever microtubules, provide good targets for modulators of such activity. Without being bound by a particular theory, it is believed that microtubule depolymerizing or severing activity is critical for normal formation and/or function of the mitotic spindle. Thus, agents that modulate (e.g., upregulate, downregulate, or completely inhibit) depolymerization or severing activity are expected to have a significant activity on progression of the cell cycle (e.g. acting as potent anti-mitotic agents).

This invention thus provides, in one embodiment, assays for identifying an agent that modulates microtubule depolymerization. The assays involve contacting a polymerized microtubule with a microtubule severing protein or a microtubule depolymerizing protein in the presence of an ATP or a GTP and the "test" agent; and detecting the formation of tubulin monomers, dimers, or oligomers. The microtubule can be labeled with any of a variety of labels, however in a preferred embodiment, it is labeled with DAPI. The formation of tubulin monomers, dimers, or oligomers can be detected by any of a wide variety of methods including, but not limited to changes in DAPI fluorescence, fluorescent resonance energy transfer (FRET), centrifugation, and the like. The microtubules are preferably microtubules that are either naturally stable (e.g., axonemal microtubules) or microtubules that have been stabilized (e.g., by contact with an agent such as paclitaxel, a paclitaxel analogue, or a non-hydrolyzable nucleotide GTP analogue such as guanylyl-($\alpha,\beta$)-methylene diphosphate (GMPCPP)).

The assays can be run in solution or in solid phase (i.e. where one or more assay components are attached to a solid surface. In one embodiment, of solid-phase assays, the microtubule is attached to the surface e.g., by direct binding or by binding with an agent such as an inactivated microtubule motor protein, an avidin-biotin linkage, an anti-tubulin antibody, a microtubule binding protein (MAP), or a polylysine. The microtubule severing protein or microtubule depolymerizing protein is preferably a katanin, a p60 subunit of a katanin, an XKCM1, or an OP18 polypeptide. In a particularly preferred embodiment, the microtubule severing protein is a katanin or a p60 subunit of a katanin as described herein.

It was also a discovery of this invention that the katanin p60 subunit exhibits both the ATPase and microtubule severing activity observed in katanin. The p60 subunit thus provides a good target for screening for potential therapeutic lead compounds. Thus, in another embodiment, this invention provides methods screening for (identifying) a therapeutic lead compound that modulates depolymerization or severing of a microtubule system. The methods involve providing an assay mixture comprising a katanin p60 subunit and a microtubule, contacting the assay mixture with a test compound to be screened for the ability to inhibit or enhance the microtubule-severing or ATPase activity of the p60 subunit; and detecting specific binding of the test compound to said p60 subunit or a change in the ATPase activity of the p60 subunit. The detecting can be by any of a wide variety of methods including, but not limited to detecting ATPase activity using malachite green as a detection reagent. Binding activity can be easily detected in binding assays in which the p60 subunit is labeled and said test agent is attached to a solid support or conversely, the test agent is labeled and the p60 subunit is attached to a solid support. In a preferred embodiment, the ATPase assays are performed in the presence of stabilized microtubules.

The assay methods of this invention are also amendable to high throughput screening. Thus, in one embodiment, any of the methods described herein is performed in an array where said array comprises a multiplicity of reaction mixtures, each reaction mixture comprising a distinct and distinguishable domain of said array, and wherein the assay steps are performed in each reaction mixture. The array can take a number of formats, however, in one preferred format, the array comprises a microtitre plate, preferably a microtitre plate comprising at least 48 and more preferably at least 96 reaction mixtures. The test agent can be one of a plurality of agents and each reaction mixture can comprise one agent of the plurality of agents.

In addition, this invention provides for polypeptides having microtubule severing activity. The polypeptides comprise an isolated p60 subunit of a katanin, where the p60 subunit is encoded by a nucleic acid that hybridizes under stringent conditions with a nucleic acid that encodes the katanin p60 amino acid sequence (SEQ ID NO:1). In a particularly preferred embodiment, the polypeptide is the polypeptide of SEQ ID NO:1 or the polypeptide of SEQ ID NO:1 having conservative substitutions. The polypeptide can comprise at least 8 contiguous amino acids from a polypeptide sequence encoded by a nucleic acid as set forth in SEQ ID NO:1, where the polypeptide, when presented as an antigen, elicits the production of an antibody that specifically binds to a polypeptide sequence encoded by a nucleic acid as set forth in SEQ ID NO: 1; and the polypeptide does not bind to antisera raised against a polypeptide encoded by a nucleic acid sequence as set forth in SEQ ID NO:1, that has been fully immunosorbed with a polypeptide encoded by a nucleic acid sequence as set forth in SEQ ID NO: 1. In a most preferred embodiment, the polypeptide is polypeptide of SEQ ID NO:1.

This invention also provides an isolated nucleic acid that encodes a katanin p60 subunit having microtubule severing activity. The nucleic acid preferably comprises a nucleic acid that specifically hybridizes with a nucleic acid that encodes the polypeptide of SEQ ID NO:1 under stringent conditions. The nucleic acid preferably encodes a polypeptide of SEQ ID NO:1 or conservative substitutions thereof. The katanin p60 encoding nucleic acid can be operably linked to a promoter (e.g. a baculovirus promoter) and may be present in a vector.

In another embodiment, this invention provides methods of screening for an agent that alters microtubule polymerization, or depolymerization, or severing. The methods involve providing labeled tubulin; contacting the labeled tubulin with the test agent to produce contacted tubulin; and comparing the fluorescence intensity or pattern of the contacted tubulin with the fluorescence intensity or pattern of labeled tubulin that is not contacted with the test agent where a difference in fluorescence pattern or intensity between the contacted and the not contacted tubulin indicates that the agent alters microtubule polymerization, or depolymerization, or severing. In particularly preferred embodiments, the labeled tubulin is in the form of tubulin monomers, tubulin dimers, tubulin oligomers, or a microtubule. In some embodiments, the microtubule is attached to a solid surface (e.g., by binding with an agent selected from the group consisting of an inactivated microtubule motor protein, an avidin-biotin linkage, an anti-tubulin antibody, a microtubule binding protein (MAP), a polyarginine, a polyhistidine, and a polylysine). Preferred labels include DAPI, ANS, Bis-ANS, ruthenium red, cresol violet, and DCVJ, with DAPI being most preferred. In some embodiments, the "contacting" step can further comprise contacting the tubulin with a microtubule depolymerizing protein or a microtubule severing protein. Preferred microtubule severing or a microtubule depolymerizing proteins include, but are not limited to katanin, a p60 subunit of a katanin, an XKCM1, and a OP18 polypeptide. A preferred p60 subunit of a katanin is a polypeptide of SEQ ID NO: 1. The method can further involve listing the agents that alter microtubule polymerization, depolymerization, or severing into a database of therapeutic lead compounds that act on the cytoskeletal system. This method can be performed in various array embodiments as described herein.

This invention also provides kits for practice of any of the methods described herein. In one embodiment, the kits comprise one or more containers containing an isolated microtubule severing protein or a microtubule depolymerizing protein. The kit can further comprise a polymerized microtubule labeled with DAPI. The microtubule can be stabilized by contact with paclitaxel or a paclitaxel derivative. The microtubule can also optionally be attached to a solid surface (e.g., by binding with an inactivated motor protein). The microtubule severing protein or microtubule depolymerizing protein is preferably selected from the group consisting of a katanin, a p60 subunit of a katanin, an XKCM1, and a OP18 polypeptide. In a particularly preferred embodiment, the microtubule severing protein is a katanin or a p60 subunit of a katanin.

DEFINITIONS

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences, as well as the sequence explicitly indicated.

Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol Chem.* 260: 2605–2608; Cassol et al. (1992); and Rossolini et al, (1994) *Mol Cell Probes* 8: 91–98). The term nucleic acid is used interchangeably with gene, cDNA, and mRNA encoded by a gene.

The terms "polypeptide," "peptide," and "protein" are used interchangeably herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR §1.822(b)(4). Furthermore, it should be noted that a dash at the beginning or end of an amino acid residue sequence indicates either a peptide bond to a further sequence of one or more amino acid residues or a covalent bond to a carboxyl or hydroxyl end group.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (1), Leucine (L), Methionine (M), Valine (V); and
6) Phenylalanine (F), Tyrosine (Y), Tryptophan (W).

The terms "isolated" and "biologically pure" refer to material which is substantially or essentially free from components which normally accompany it as found in its native state. However, the term "isolated" is not intended to refer to the components present in an electrophoretic gel or other separation medium. An isolated component is free from such separation media and in a form ready for use in another application or already in use in the new application/milieu.

The terms "identical," percent "identity," and percent "homology" in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% or even at least 98% amino acid residue identity across a window of at least 30 nucleotides, preferably across a window of at least 40 nucleotides, more preferably across a window of at least 80 nucleotides, and most preferably across a window of at least 100 nucleotides, 150 nucleotides, 200 nucleotides or greater, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Natl. Acad Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (See generally, Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J Mol. Evol.* 3 5:3 51–360. The method used is similar to the method described by Higgins & Sharp (1989) CABIOS 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol Biol.* 215:403–410. Software for performing BLAST analyses is publicly available through the National Center for Biotechnology Information (http://www.nebi.rilm.nih.gov/). This algorithm involves first identifying high scoring sequence pairs (HSPs) by identifying short words of length "W" in the query sequence, which either match or satisfy some positive-valued threshold score "T" when aligned with a word of the same length in a database sequence. "T" is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity "X" from its maximum achieved value; the cumulative score goes to zero or below, due to the accumulation of one or more negative-scoring residue alignments; or the end of either sequence is reached. The BLAST algorithm parameters "W," "T," and "X" determine the sensitivity and speed of the alignment. The BLAST program uses as defaults a wordlength ("W") of 11, the BLOSUM62 scoring matrix (See Henikoff & Henikoff (1989) *Proc. Natl. Acad Sci USA* 89:10915) alignments (B) of 50, expectation (E) of 10, M=5, N=−4, and a comparison of both strands.

In addition to calculating percent sequence identity, the BLAST algorithm also performs a statistical analysis of the similarity between two sequences (See, e.g., Karlin & Altschul (1993) *Proc. Natl. Acad Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrases "hybridizing specifically to," "specific hybridization," and "selectively hybridize to," refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization experiments such as Southern and Northern hybridizations are sequence dependent, and are different under different environmental parameters. An extensive guide to the hybridization of nucleic acids is found in Tijssen (1993) *Laboratory Techniques in Biochemistry and Molecular Biology-Hybridization with Nucleic Acid Probes* part I chapter 2 Overview of Principles of Hybridization and the Strategy of Nucleic Acid Probe Assays, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (See, Sambrook et al. (1989) *Molecular Cloning—A Laboratory Manual* (2nd ed.) Vol. 1–3, Cold Spring Harbor Laboratory, Cold Spring Harbor Press, N.Y., for a description of SSC buffer). Often, a high stringency wash is preceded by a low stringency wash to remove background probe signal. An example medium stringency wash for a duplex (e.g., of more than 100 nucleotides), is 1×SSC at 45° C. for 15 minutes. An example low stringency wash for a duplex (e.g., of more than 100 nucleotides), is 4-6× SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, for example, when a copy of a nucleic acid is created using the maximum codon degeneracy permitted by the genetic code.

The terms "katanin" or "katanin p60 subunit" refer to katanin and the katanin p60 subunit as described herein, in the references cited and in the sequence listings. The terms also include proteins having substantial amino acid sequence identity with katanin or the katanin p60 subunit sequences provided herein that exhibit ATPase and microtubule severing activity.

The terms "taxol" and "taxol derivatives or analogues refer to the drug taxol known generically as paclitaxel (NSC number: 125973). Paclitaxel (taxol) derivatives and analogues show similar microtubule-stabilizing activity. Preferred derivatives include taxotere and others.

Depolymerized microtubule components are defined so as to include the products of microtubule depolymerization or severing, and include tubulin monomers, dimers and oligomers.

The term "test agent" refers to an agent that is to be screened in one or more of the assays described herein. The agent can be virtually any chemical compound. It can exist as a single isolated compound or can be a member of a chemical. (e.g., combinatorial) library. In a particularly preferred embodiment, the test agent will be a small organic molecule.

The term small organic molecules refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The terms "label" or "detectable label" are used herein to refer to any composition detectable by spectroscopic, photochemical, biochemical, immunochemical, electrical, optical or chemical means. Such labels include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE DRAWINGS

FIGS. 1A and 1B show the sequence analysis of p60 katanin. FIG. 1A: Predicted protein sequence of the *S. purpuratus* katanin p60 subunit (SEQ ID NO:1; GENBANK AF052191). Sequences obtained by direct peptide microsequencing are underlined. Differences between the predicted peptide sequence and that obtained by direct sequencing are indicated by doubled underlines (S95 was reported as F, H99 was reported as P, and P138 was reported as T). The Walker A (P-loop) motif is shaded. FIG. 1B: Amino acid sequence alignment of the p60 AAA domain (SEQ ID:NO4) with AAA members mei-1 (SEQ ID NO:5; *C. elegans,* GenBank L25423), Suglp (SEQ ID NO:6; *S. cerevisiae,* GenBank X66400), ftsH (SEQ ID NO:7; *E. coli,* GenBank M83138), Paslp (SEQ ID NO:8; *S. cerevisiae,* GenBank M58676), and NSF (SEQ ID NO:9; *C. longicaudatus,* GenBank X15652). Identical residues are shaded black, residues conserved in >60% of the shown members are shaded gray. Left hand numbering indicates the amino acid residue in the corresponding sequence. Alignment was performed using PILEUP (Genetics Computer Group) and the output was shaded using MACBOXSHADE.

FIGS. 2A and 2B show the sequence analysis of p80 katanin. FIG. 2A: Predicted protein sequence of the *S. purpuratus* katanin p80 subunit (SEQ ID NO:2; GENBANK AF052433). Sequences obtained by direct peptide microsequencing are underlined. Differences between the predicted peptide sequence and that obtained by direct peptide sequencing, or differences found between 2 different p80 cDNA clones are indicated by double underlines. FIG. 2B: Amino acid sequence alignment of the WD40 repeat region of p80 (SEQ ID NO:10) with a putative human ortholog of p80 (SEQ ID NO:11; *Homo sapiens l p*80, GenBank AF052432), TFIID (SEQ ID NO:12; *Homo sapiens,* GenBank U80191), and putative serine/threonine kinase PkwA (SEQ ID NO: 13; *Thermomonospora curvata,* GenBank P49695). Identical residues are shaded black, residues found in at least 2 sequences are shaded in grey. Left hand numbering indicates the amino acid residue in the corresponding sequence. Alignment was performed using PILEUP (Genetics Computer Group) and the output was shaded using MACBOXSHADE.

FIG. 5A shows ATPase activities of 0.04 µM p60 katanin (squares) and co-expressed p60/p80 (circles) determined at various microtubule concentrations as described in the Experimental Procedures. Both p60 katanin and p60/p80 show similar patterns of microtubule stimulation, with p60 katanin having approximately one half of the maximally stimulated ATPase activity of p60/p80. The insert in the upper right shows the stimulation of ATPase activity at low (0–2 µM) microtubule concentration. FIG. 5B shows microtubule severing activity of recombinant katanin subunits. Taxol-stabilized, rhodamine-labeled microtubules were adsorbed onto the surface of a microscope perfusion chamber, and then recombinant katanin subunits were introduced. The time elapsed after perfusing p60/p80 (0.1 µM), p60 (0.1 µM), or p80 (0.5 µM) is shown. The recombinant co-expressed p60/p80 and p60, but not p80, can sever and disassemble microtubules. Scale bar, 10 µm. FIG. 5C shows quantitative measurement of microtubule disassembly using a DAPI fluorescence assay. MT indicates microtubules (2 µM) without added protein, and tubulin indicates microtubules that had been depolymerized by treatment with 10 mM $CaCl_2$ on ice for 1.5 hr. p60 katanin and p60/p80 were added at 0.2 µM concentration, and the fluorescence change as a function of time after protein addition is shown. p80 did not cause a change in fluorescence that was different from that shown for microtubules alone.

DETAILED DESCRIPTION

I. Introduction

Figure 3A:
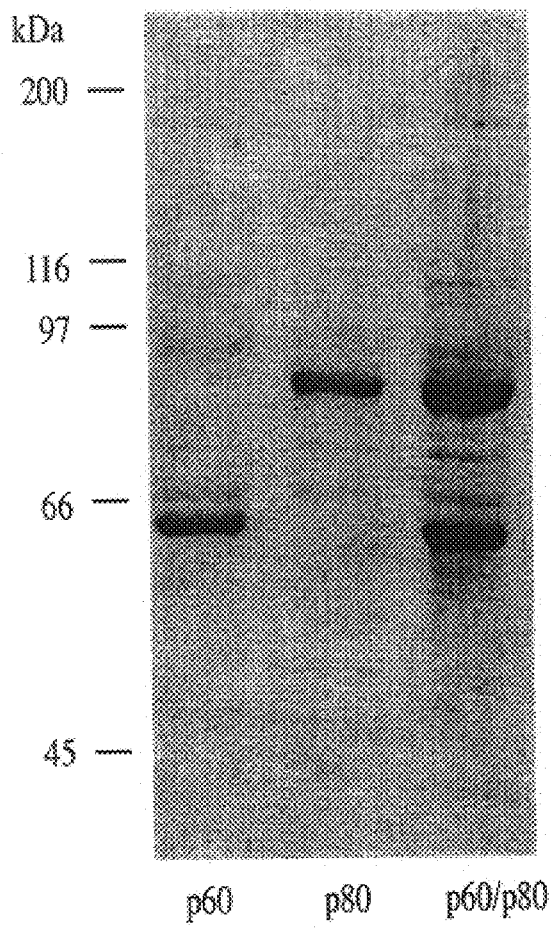
FIG. 3 illustrates the results of expression and purification of recombinant katanin subunits. Panel A shows Coomassie-stained SDS-PAGE analysis of expressed katanin subunits. 6×His-tagged (SEQ ID NO: 14) katanin subunits were purified from lysates of baculovirus-infected insect cells by binding to $Ni^{2+}$-NTA Superflow followed by elution with imidazole, as described in the Experimental Procedures. Cells were infected with either p60 virus alone, p80 virus alone, or coinfected with equal amounts of p60 and p80 viruses. Panel B shows immunoprecipitation performed on extracts of insect cells coinfected with p60- and p80expressing baculoviruses using affinity-purified p60 antibody crosslinked to protein A agarose. Proteins bound to the resin were analyzed by SDS-PAGE followed by staining with Coomassie. This immunoprecipitate shows that baculovirus-expressed p60 and p80 form a complex with equal stoichiometry.

This invention provides assays for the identification of agents that modulate the activity of microtubule depolymerizing or severing proteins. The assays generally involve contacting a polymerized microtubule with a microtubule severing or depolymerizing protein (e.g., XKCM1, OP18, katanin, etc.) the presence of a test agent and a chemical energy source (e.g., ATP or GTP). The effect of the agent on the depolymerization or severing of the microtubules is then detected typically by detecting the formation of microtubule degradation components (e.g., tubulin monomers, tubulin dimers, or tubulin oligomers). Test agents that alter the amount and or rate of depolymerization or severing of microtubules as compared to one or more control assays are identified as modulators of microtubule depolymerizing or severing activity.

It was a discovery of this invention that certain proteins that either depolymerize or sever microtubules, provide good targets for modulators of normal mitotic spindle formation. Without being bound by a particular theory, it is believed that microtubule depolymerizing or severing activity is critical for normal mitotic spindle formation and/or function. Agents that modulate (e.g., upregulate, downregulate, or completely inhibit) depolymerization or severing activity are expected to have a significant activity on progression of the cell cycle. Thus, for example, inhibitors of microtubule depolymerization or severing will act as potent antimitotic agents.

Anti-mitotic agents are useful in a wide variety of contexts. As powerful anti-mitotics or anti-meiotics, the inhibitors of microtubule depolymerizing or severing activity identified by the screening (assay) methods described herein, will have a wide variety of uses, particularly in the treatment (e.g., amelioration) of pathological conditions characterized by abnormal cell proliferation. Such conditions include, but are not limited to: fungal infections, abnormal stimulation of endothelial cells (e.g., atherosclerosis), solid tumors and tumor metastasis, benign tumors (for example, hemangiomas, acoustic neuromas, neurofibromas, trachomas, and pyogenic granulomas), vascular malfunctions (e.g., arterio-venous malformations), abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal overgrowth, corneal graft rejection, neuroscular glaucoma, Oster Webber syndrome, and the like.

The inhibitors of microtubule depolymerization or severing will also have a variety of in vitro uses as well. For example, they can be used to freeze cells in a particular stage of the cell cycle for a variety of purposes (e.g., in the preparation of samples for of histological examination), in the isolation of nucleic acids from a particular stage of the cell cycle, and so forth.

The modulators identified by the assays of this invention are preferably characterized by specificity to the target microtubule depolymerizing or severing proteins or the pathways characteristic of the activity of these proteins. They therefor provide novel lead compounds for the development of highly specific inhibitors for depolymerizing and/or microtubule severing protein families and subfamilies, thus allowing for precise chemical intervention.

IL Assays for the Detection of Microtubule Depolymerization Modulators.

A) Depolymerization Assay

In one embodiment, this invention provides assays for the detection/identification of agents that have activity in modulating the depolymerization or severing of microtubules. The assays generally involve contacting a polymerized microtubule with a microtubule severing protein or a microtubule depolymerizing protein in the presence of a chemical energy source (e.g., ATP or GTP) and said agent; and detecting and/or quantifying the formation of microtubule degradation products (e.g., tubulin monomers). Agents that inhibit the activity of the microtubule depolymerizing or severing proteins will inhibit the breakdown of the polymerized microtubules thereby delaying the formation of or reducing the quantity of tubulin monomers or oligomers. Thus a decrease in the rate of formation or amount of tubulin monomer or an increase in the ratio of tubulin polymer (microtubule) to tubulin monomer indicates an inhibitory modulating effect of the agent. Conversely, an increase in the rate of formation or amount of tubulin monomer or an increase in the ratio of tubulin polymer (microtubule) to tubulin monomer indicates a microtubule stabilizing modulating effect of the agent.

The increase or decrease is determined by reference to one or more controls. A control is essentially an identical assay that either lacks the test agent or contains a "reference" agent that has a known activity. Assays lacking any test agent whatsoever act as negative controls, while assays utilizing an agent that has known modulating activity act as positive controls.

In a preferred embodiment, the assay is scored as positive (i.e., the agent has activity modulating a microtubule depolymerizing or severing protein) when there is a significant difference between the negative control and test assay and/or when there is no significant difference between the positive control and test assay. The significant difference is preferably a statistically significant difference, more preferably at least about a 10% difference, and most preferably at least about a 20%, 30%, 50% or 100% difference.

The assays can be performed in solution or in solid phase (i.e., with one or more components of the assay attached to a solid surface) as described below. One particularly preferred embodiment is described herein in Example I. The various components of the assay are described below.

B) Binding Assays

In another embodiment, this invention provides binding assays to identify agents that inhibit binding of depolymerizing or severing proteins to microtubules or for agents that specifically bind to the microtubule depolymerizing or severing polypeptide or polypeptide subunit.

In preferred binding assays, the ability of the test agent to specifically bind to the depolymerizing or severing protein is assayed. In a particularly preferred embodiment, the ability of the test agent to specifically bind to a katanin p60 domain is assayed.

There are a wide variety of formats for binding assays. In one embodiment, the depolymerizing or severing protein or protein subunit is immobilized on a surface and contacted with the test agent or conversely test agent(s) are immobilized on a surface and specific binding of the protein or protein subunit is assayed. Binding is most easily detected where the moiety in solution (test agent or depolymerizing or severing protein) is labeled and after the contacting and washing off of unbound agents, identification of the labeled moiety associated with the support suggests binding.

Solution phase binding assays are also known to those of skill in the art. For example, in one embodiment, the binding assay is a cosedimentation assay. In this (pelleting) assay, when the test agent binds to the microtubule severing or depolymerizing protein or protein subunits, the bound agent and protein will cosediment when centrifuged. Unbound polypeptide and test agent will either sediment at a different rate or remain fully in solution.

Methods of performing various binding assays can be found in copending application U.S. S. No. 60/057,895 filed on Sep. 4, 1997. For a general description of different formats for protein binding assays, including competitive binding assays and direct binding assays (See, Stites and A.

Terr (1991) *Basic and Clinical Immunology*, 7th Edition; Maggio (1980) *Enzyme Immunoassay*, CRC Press, Boca Raton, Fla.; and Tijssen (1985) *Practice and Theory of Enzyme Immunoassays*, in *Laboratory Techniques in Biochemisty and Molecular Biology*, Elsevier Science Publishers, B. V. Amsterdam).

C) ATPase Assay

It was a discovery of this invention that the katanin p60 subunit is a new member of the AAA family of ATPases and that expressed p60 has microtubule-stimulated ATPase and microtubule-severing activities in the absence of the p80 subunit. Thus, in another embodiment, this invention provides assays for agents that modulate the ATPase activity of a katanin p60 subunit.

ATPase assays are well known to those of skill in the art. In one preferred embodiment, the assay can be performed according to the methods described by Kodama et al. (1986) *J. Biochem.* 99: 1465–1472. This assay, described in detail in Example 1, is performed with the test agent present and the results are compared to negative and/or positive control assays to determine the ability of the test agent to alter (modulate) p60 ATPase activity.

D) Solid Phase Assays

In one embodiment, the assays of this invention can be performed in solid phase where one or more components of the assay is attached to a solid surface. Solid phases assays, one or more components of the assay is attached to a solid surface. Virtually any solid surface is suitable, as long as the surface material is compatible with the assay reagents and it is possible to attach the component to the surface without unduly altering the reactivity of the assay components. It is recognized that some components show reduced activity in solid phase, but this is generally acceptable so long as the activity is sufficient to detect and/or quantify depolymerization or severing activity of the subject protein.

Solid supports include, essentially any solid surface, such as a glass bead, planar glass, controlled pore glass, plastic, porous plastic metal, or resin to which the molecule may be adhered. One of skill will appreciate that the solid supports may be derivatized with functional groups (e.g., hydroxyls, amines, carboxyls, esters, and sulfhydryls) to provide reactive sites for the attachment of linkers or the direct attachment of the component(s).

Adhesion of the assay component (e.g., microtubule(s)) to the solid support can be direct (i.e., the microtubule directly contacts the solid support) or indirect (i.e., a particular compound or compounds are bound to the support, and the assay component binds to this compound or compounds rather than to the solid support). The component can be immobilized either covalently (e.g., utilizing single reactive thiol groups of cysteine for anchoring protein components (Colliuod et al. (1993) *Bioconjugate Chem.* 4, 528–536)), or non-covalently but specifically (e.g., via immobilized antibodies or other specific binding proteins (Schuhmann et al. (1991), *Adv. Mater.* 3: 388–391; and Lu et al. (1995), *Anal. Chem.* 67: 83–87), the biotin/streptavidin system (Iwane et al. (1997) *Biophys. Biochem. Res. Comm.* 230: 76–80), or metal-chelating Langmuir-Blodgett films (Ng et al. (1995) *Langmuir* 11: 4048–4055; Schmitt et al. (1996) *Angew. Chem. Int. Ed. Engl.* 35: 317–320; Frey et al. (1996) *Proc. Natl. Acad. Sci. USA* 93:4937–4941; and Kubalek et al. (1994) *J Struct. Biol.* 113:117–1231) and metal-chelating self-assembled monolayers (Sigal et al. (1996) *Analytical Chem.*, 68: 490–497) for binding of polyhistidine fusion proteins.

In a preferred embodiment, the microtubule(s) are immobilized by attachment to an inactivated microtubule motor protein, by an avidin biotin linkage (preferably with the biotin on the microtubule and the avidin on the surface), by an anti-tubulin antibody, by a microtubule binding protein. (MAP), by an amino silane, a polylysine, or through interaction with a polycationic surface.

By manipulating the solid support and the mode of attachment of the assay component to the support, it is possible to control the orientation of the assay component (s). For example, copending application U.S. S No. 60/057, 929, filed on Sep. 4, 1997, describes the use of an arginine tail to attach cytoskeletal proteins to a mica film.

In one preferred embodiment, the microtubules are immobilized by coating the surface (e.g., a flow cell) with either n-ethylmaleimide (NEM)-treated Xenopus egg extract (6 mg/ml protein treated with 10 mM NEM for 10 minutes followed by addition of 100 mM dithiothreitol, a treatment that inactivates severing activity) or *Escherichia coli*-expressed KAR3 protein (which binds microtubules in a nucleotide-independent manner). After washing out unbound protein, the stabilized microtubules (e.g., 100 µg/ml in BR80, 20 µM taxol) are perfused onto the surface and allowed to bind. After washing out unbound microtubules samples to be tested can be contacted to the surface (e.g., perfused into a flow cell).

E) High-throughput Screening of Candidate Agents that Modulate Microtubule Depolymerizing or Severing Proteins Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

i) Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed at the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (See, e.g., U.S. Pat. No. 5,010,175, Furka (1991) *Int. J Pept. Prot. Res.,* 37: 487–493; and Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad Sci. USA* 90: 6909–6913), vinylogous polypeptides (Hagihara et al. (1992) *J Amer. Chem. Soc.* 114: 6568), nonpeptidal peptidomimetics with a Beta- D- Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658); See, generally, Gordon et al., (1994) *J. Med Chem.* 37:1385), nucleic acid libraries (See, e.g., Strategene, Corp.), peptide nucleic acid libraries (See, e.g., U.S. Pat. No. 5,539,083) antibody libraries (See, e.g., Vaughn et al. (1996) *Nature Biotechnology,* 14(3): 309–314), and PCT/US96/10287), carbohydrate libraries (See, e.g., Liang et al. (1996) *Science,* 274: 1520–1522, and U.S. Pat. No. 5,593,853), and small organic molecule libraries (See, e.g., benzodiazepines, Baum (1993) C&EN, January 18, page 33; isoprenoids U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (See, e.g., 357 NIPS, 390 NTS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (See, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

ii) High Throughput Assays of Chemical Libraries

Any of the assays for compounds modulating the activity of microtubule depolymerizing or severing proteins (or other agents) described herein are amenable to high throughput screening. As described above, in a preferred embodiment, the assays screen for agents that enhance or inhibit the activity of katanin, XKCM1, or OP18. Preferred assays detect the rate or amount of depolymerization of microtubules into tubulin monomers, tubulin dimers, or tubulin oligomers.

High throughput implementation of the assays described herein can be implemented with, at most, routine modification of the assays format (e.g., for compatibility with robotic manipulators, large plate readers, and the like). Various high throughput screening systems (e.g., for protein binding, nucleic acid binding, etc.) are described in U.S. Pat. Nos. 5,559,410, 5,585,639, 5,576,220, and 5,541,061.

In addition, high throughput screening systems are commercially available (See, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

III) Assay Components

A) Polymerized microtubules

As indicated above, the assays of this invention utilize polymerized microtubules, which, in the presence of a depolymerizing protein or severing protein are depolymerized or cleaved to produce tubulin monomers or oligomers. When the depolymerizing or severing proteins are inhibited, the formation of tubulin monomers or oligomers is inhibited.

Virtually any microtubules can be used for the assays of this invention. Means of obtaining such microtubules are well known to those of skill in the art. Tubulin is available commercially or can be isolated from a wide variety of sources (e.g., plants, animal tissues, oocytes, etc.) For example, tubulin can be isolated from Arabidopsis cells in stationary phase (day 10 to 11) cultured cells (200 to 500 gm fresh weight) by DEAE-Sephadex A50 chromatography as described by Morejohn et al. (1985). *Cell Biol. Int. Rep.* 9(9): 849–857 with modifications described in Bokros et al. (1993), *Biochemistry* 32(13): 3437–3447. Briefly, Arabidopsis cells are homogenized in an isolation buffer (IB) consisting of 50 mM PIPES-KOH, pH 6.9, 1 mM EGTA, 0.5 mM $MgSO_4$, 1 mM DTT and 0.1 mM GTP, supplemented with 50 mg/mL Na-p-tosyl-L-arginine methyl ester (TAME), and 5 mg/ML each of pepstatin A, leupeptin hemisulfate, and aprotinin. The cell homogenate is subjected to DEAE-Sephadex A50 chromatography for tubulin isolation. Ammonium sulfate precipitates of DEAE-isolated tubulin can be aliquoted and stored at −80° C. until use.

Microtubules can be purified to homogeneity by a single taxol-induced microtubule polymerization step in IB supplemented with 1 mM GTP as described previously (Bokros et al. (1993), *Biochemistry* 32(13): 3437–47). Briefly, samples of DEAE-isolated tubulin are thawed and resuspended in IB supplemented with 1 mM DTT and 1 mM GTP, and clarified by centrifugation for 1 hr at 100,000×g (2° C.) in a Beckman TL-100 ultracentrifuge (TLA-100 rotor). Clarified tubulin is polymerized with a twofold molar excess of taxol in a microtubule assembly buffer composed of IB, 1 mM DTT, 1 mM GTP and 1% DMSO. Assembly of microtubules was performed by gradual temperature ramping from 2° C. to 25° C. over a 2-hour period. Polymer is collected by centrifugation for 45 min at 30,000×g at 25° C. through a cushion of 20% (w/v) sucrose in assembly buffer.

In a preferred embodiment, the tubulin/microtubules are isolated from an animal tissue (e.g., brain tissue) according to the methods of Hyman et al. (1991) *Meth Enzy.,* 196: 478–485. The brain tubulin can be modified with tetramethylrhodamine or fluorescein N-hydroxysuccinimide ester (Molecular Probes, Inc., Eugene, Oreg.) as described by Hyman et al. (1991) supra.

Most microtubules are in a state of flux, undergoing assembly and disassembly. In a preferred embodiment of the assays of this invention microtubules are utilized that are stabilized as essentially intact microtubules. This can be accomplished by using microtubules that are naturally stable (e.g., axonemal microtubules) or by treating the microtubules so that they are stabilized. Methods of stabilizing microtubules are well known to those of skill in the art and include, but are not limited to the use of stabilizing agents such as paclitaxel and paclitaxel derivatives (e.g., taxotere), non-hydrolyzable nucleotide (e.g., GTP) analogues (e.g. guanylyl-($\alpha,\beta$)-methylene diphosphate (GMPCPP)), and the like.

In a preferred embodiment, taxol-stabilized microtubules, are prepared by polymerizing tubulin (2–10 mg/ml) at 37° C. for 45 minutes in BRB80 (80 mM PIPES [pH 6.8], 1 mM $MgCl_2$, 1 mM EGTA) containing 1 mM GTP and 10% dimethyl sulfoxide (DMSO). Taxol is then added to a concentration of 20 $\mu$M.

GMPCPP-stabilized microtubules are prepared by incubating tubulin in the above, buffer, substituting 0.5 mM GMPCPP for GTP. The GMPCPP microtubules can be stored at room temperature without taxol and are preferably used within 1 day after preparation.

B) Assay Reaction Mixture

The assays of this invention are performed in a reaction mixture that provides the components necessary for microtubule depolymerizing or microtubule severing activity of the subject protein (e.g., katanin, XKCM1, OP18 etc.) and that are compatible with the enzymatic activity of the subject proteins. Typically the reaction mixture comprises an appropriate buffer (e.g., HEPES, pH 6.5–8.0) and an energy supplying molecule such as guanosine triphosphate (GTP) for microtubule depolymerizing proteins or adenosine triphosphate (ATP) for severing molecules such as katanin. One preferred assay,mixture is described in Example 1.

C) Microtubule Depolymerizing and Microtubule Severing Agents

As indicated above, the assays of this invention essentially detect the activity of a test agent on a microtubule depolymerizing or microtubule severing polypeptide. Microtubule depolymerizing polypeptides such as OP18 (Belmont et al. (1990) *Cell,* 62: 579–589) and XKCM1 (Walczak et al. (1996) *Cell,* 83: 37–47) increase the frequency of catastrophes (transitions of a microtubule from a growing to a shrinking state) and thus promote disassembly of microtubules from their ends.

In contrast to microtubule depolymerizing proteins, other proteins, such as katanin, promote the disassembly of microtubules by generating internal breaks within a microtubule and are referred to as microtubule severing proteins (See, e.g., Vale (1991) *Cell* 64: 827–839; Shiina et al. (1994) *Science* 266: 282–285; Shiina et al. (1992) *EMBO J.* 11: 4723–4731; and McNally and Vale (1993) *Cell,* 75: 419–429).

Preferred microtubule depolymerizing proteins for the methods of this invention include, but are not limited to XKCM1, and OP18, while preferred microtubule severing proteins include katanin.

i) Katanin

Katanin, a heterodimer of 60 kDa and 80 kDa subunits purified from sea urchin eggs, is unique among the known microtubule and actin severing proteins in that it disrupts contacts within the polymer lattice by using energy derived from ATP hydrolysis (McNally and Vale (1993) *Cell,* 75: 419–429). Katanin acts substoichiometrically, as one molecule of katanin can release several tubulin dimers from a microtubule. Katanin does not appear to proteolyze or modify tubulin, since the tubulin released from the disassembly reaction is capable of repolymerizing (McNally and Vale (1993) *Cell,* 75: 419–429). The mechanism of microtubule severing by katanin, however, is not understood.

Katanin-catalyzed microtubule severing and disassembly could potentially be involved in several changes in the microtubule cytoskeleton observed in vivo. Recent studies have-shown that katanin is concentrated at the centrosome in a microtubule-dependent manner in sea urchin embryos (McNally et al. (1996) *J Cell Sci.* 109: 561–567). One phenomenon that could require disassembly of microtubules at the centrosome is the poleward flux of tubulin in the mitotic spindle (Mitchison (1989) *J Cell Biol.* 109: 637–652). The disassembly of microtubule minus ends at the spindle pole during poleward flux could be driven by katanin, or katanin could simply allow depolymerization by uncapping microtubule minus ends that are docked onto γ-tubulin ring complexes (Zheng et al. (1995) *Nature* 378: 578–583; Moritz et al. (1995)*Nature* 378: 638–640). Another possible role for katanin at the centrosome is in promoting the release of microtubules from their centrosomal attachment points. Microtubules are nucleated from γ-tubulin ring complexes at the centrosome (Joshi et al., (1992) and Moritz et al. (1995) *Nature* 378: 63 8–640), but release of microtubule minus ends has been observed indirectly in Dictyostelium (Kitanishi-Yumura et al. (1987) *Cell Motil. Cytoskeleton* 8: 106–117) and directly in PtK1 cells (Keating (1997) *Proc. Natl. Acad. Sci. USA,* 94:5078–5083) and Xenopus egg extracts (Belmont et al. (1990) *Cell* 62: 579–589). Finally, katanin could accelerate the rapid disassembly of the interphase microtubule network at the G2/M transition (Zhai et al. (1996) *J. Cell Biol.* 135: 201–214) by severing cytoplasmic microtubules, which would increase the number of free microtubule ends from which depolymerization could occur. Regardless of the particular mode of activity, modulation of katanin activity will have profound effects on the cell cycle.

The amino acid and nucleic acid sequences of the p60 and p80 subunits of katanin are provided in FIGS. 1A and 2A (See also SEQ ID NO:1 and SEQ ID NO:2). It was a discovery of this invention that the microtubule severing activity resides entirely in the p60 subunit. Thus the assays of this invention can be practiced either with the heterodimeric katanin or with a p60 subunit alone.

The p60 and/or p80 subunits of katanin can be purified (e.g., from sea urchin eggs, e.g., eggs from *Strongylocentrotus purpuratus*) as described by McNally and Vale (1993) *Cell,* 75: 419–429. Alternatively, either or both subunits can be recombinantly expressed and purified as described below and in Example 1.

ii) XKCM1

XKCM1 (for Xenopus kinesin central motor 1) is a motor protein essential for mitotic spindle assembly in vitro. XKCM1 localizes to centromeres and appears to regulate the polymerization dynamics of microtubules. The isolation of an XKCM1 clone is described by Walczak et al. (1996) *Cell,* 84: 37–47, and a nucleic acid sequence of an XKCM1 cDNA is provided therein and in SEQ ID NO:3. Using this sequence information, XKCM1 can be expressed as described below and by Walczak et al. (1996) supra.

iii) OP18

Another microtubule depolymerizing motor protein suitable for use in the methods of this invention is OP18, also called stathmin or stathmin/op18. OP18 is described in detail by Gradin et al. (1998) *J. Cell Biol.,* 140(1):131–141, by Andersen et al. (1997) *Nature,* 389(6651):640–643, by Larsson et al. (1997) *Mol. Cell. Biol.,* 17(9):5530–5539, and by Belmont et al. (1996) *Cell,* 84(4):623–631.

iv) Other Microtubule Severing or Depolymerizing Proteins

Other microtubule depolymerizing or severing proteins include, but are not limited to elongation factor-1α (Shiina et al. (1994) *Science* 266: 282–285) and a novel homo-oligomeric protein described by Shiina et al. (1992) *EMBO J.* 11: 4723–4731.

Other microtubule depolymerizing or severing proteins can be identified with only routine experimentation. The assays used to identify microtubule depolymerizing or severing proteins are identical to the assays described herein, the only difference being that no test agent is required. A detailed example of the assay of a microtubule severing protein (katanin) is provided in McNally and Vale (1993) *Cell,* 75: 419–429. The same approach can readily be used to identify other severing or depolymerizing proteins.

IV) Detection Methods

Any detection method that allows detection and/or quantification of the amount or rate of appearance of tubulin monomers or oligomers and/or the rate of disappearance of assembled (polymerized) microtubules can be used in the assays of this invention. Preferred detection methods include, but are not limited to video microscopy; DAPI fluorescence changes, fluorescence resonance energy transfer and centrifugation.

A) Video Microscopy

In one embodiment, microtubule depolymerization or severing is detected by microscopy (visually or using a video or photographic recording device). Assays involving microscopic visualization of microtubules preferably utilize labeled (e.g., fluorescently labeled) microtubules. The microtubules are preferably immobilized on a solid support (e.g., a glass slide), and exposed to a solution containing the microtubule depolymerizing or severing protein and an a nucleoside triphosphate. The intact and depolymerized or severed microtubules can be directly visualized using a microscope. Microtubule depolymerization in the control and the assay containing the test agent can be visualized side by side or sequentially.

The microscope can optionally be equipped with a still camera or a video camera and may be equipped with image acquisition and analysis software to quantify the relative abundance of intact and fragmented microtubules.

This method can be used with essentially any label that can be visualized in a microscope. Such labels include, but are not limited to fluorescent labels (e.g., fluorescein, rhodamine, etc.), colorimetric labels, and radioactive labels (with appropriate scintillation screen), and the like. In some embodiments of the assays of this invention, the microtubules can be visualized without any label (e.g., via differential interference contrast microscopy).

An illustration of the use of video microscopy to visualize microtubule severing by katanin is provided by McNally and Vale (1993) *Cell,* 75: 419–429. In this case, the microtubules are labeled with rhodamine and the images of the severed microtubules are captured digitally.

B) DAPI Fluorescence Changes

In another embodiment, the state of microtubule polymerization can be determined by changes in fluorescence of DAPI stained microtubules. It has been shown that DAPI fluorescence intensity is higher when this dye is bound to polymerized versus free tubulin (Heusele et al. (1987) *Eur. J. Biochem.* 165: 613–620). When katanin and ATP were incubated with DAPI-labeled microtubules, a linear decrease in fluorescence intensity is observed as a function of time, reflecting the conversion of microtubules to tubulin.

Assay can thus be performed as described above with DAPI labeled stabilized microtubules. The rate or amount decrease in DAPI fluorescence is detected as described by Heusele et al. supra. The change in fluorescence with a test agent is compared to that observed in a negative and/or positive control reaction.

It was a surprising discovery of this invention that tubulin, tubulin dimers, tubulin oligomers or microtubules can be labeled with various labels such as DAPI and that the label does not interfere with the interaction of various test agents or cytoskeletal associated proteins with the labeled tubulin to a degree that would prevent assaying the impact of a test agent on microtubule polymerization, and/or depolymerization, and/or severing. Labels that can be used include, but are not limited to anilinonapthalene sulfonate (ANS) (e.g., Molecular Probes Catalogue Nos: A-47, A-50, T-53, etc.), bis-ANS (Molecular Probes Catalogue No: B-153), N-phenyl-1-naphthylene (NPN) (Molecular Probes Catalogue No: P65), DCVJ (Molecular Probes Catalogue No: D-3923), ruthenium red, and cresol violet.

C) Fluorescence Resonance Energy Transfer

The degree of microtubule polymerization/depolymerization can also be determined by fluorescent resonance energy transfer (FRET). Fluorescence resonance energy transfer, a phenomenon that occurs when two fluorophores with overlapping absorption and emission spectra are located close together (e.g., <7 nm apart) (Stryer (1978) *Ann. Rev. Biochem.,* 47: 819–846). FRET is a powerful technique for measuring protein-protein associations and has been used previously to measure the polymerization of monomeric actin into a polymer (Taylor et al. (1981) *J. Cell Biol.,* 89: 362–367) and actin filament disassembly by severing (Yamamoto et al. (1982) *J. Cell Biol.,* 95: 711–719).

In a preferred embodiment, equimolar proportions of differently labeled (e.g., fluorescein labeled and rhodamine-labeled) tubulin are combined. The fluorescence is quenched upon tubulin polymerization indicating that the tubulin-bound fluorochromes in a microtubule come in close enough proximity for energy transfer to occur. When the microtubule is depolymerized or severed, a rapid unquenching of (e.g., fluorescein) fluorescence is observed.

The rates and/or amount of fluorescence generated by a reaction with a test agent and a control can be compared. A decrease in rate or amount of fluorescence in the presence of a test agent indicates inhibitory activity on the microtubule depolymerizing or severing protein(s).

In particularly preferred embodiment, the microtubules are polymerized from a mixture of equal concentrations of fluorescein and rhodamine tubulin and diluted to 600 $\mu$/ml tubulin in BRB80 containing 20 $\mu$M taxol and the oxygen-depleting system consisting of glucose oxidase (30 $\mu$g/ml), catalase (100 mg/ml), glucose (10 mM), and dithiothreitol (10 mM) (Kishino and Yanigida (1988) *Nature* 334: 74–76). Aliquots 150 $\mu$l of these microtubules can be mixed (e.g., with samples of purified severing protein), and the fluorescence from the fluorescein (excitation 492 nm; emission 518 nm) is recorded. The reaction is preferably run with a positive and negative control. A detailed FRET assay for tubulin polymerization is found in McNally et al. (1993) *Cell,* 75: 419–429.

D) Centrifugation

Microtubule disassembly in solution can be documented in a quantitative manner by examining the relative amounts of sedimentable and nonsedimentable tubulin after incubation with the severing or depolymerizing protein (e.g., katanin) and ATP or GTP. In the absence of a modulating agent, when taxol-stabilized microtubules are incubated tithe the katanin p80 and p60 subunits and ATP, nonsedimentable tubulin is released from microtubule polymer in an approximately linear manner. The rate of release varies with microtubule depolymerizing or severing protein concentration and will be dependent on the activity of a modulating "test" agent if present.

In a preferred embodiment, fluorescent microtubules (e.g., 100–300 µg/ml tubulin) are incubated with the microtubule depolymerizing or severing protein in buffer (e.g., 20 mM HEPES (pH 7.5), 2 mM $MgCl_2$, 25 mM potassium glutamate, 0.02% Triton X-100, 250 µg/ml SBTI, and 20 µM taxol or taxol derivative) at various times. Aliquots (e.g., of 100 µl) are brought to 10 mM ADP or GDP (to stop the severing or depolymerizing reaction) and sedimented (e.g., at 228,000 ×g for 10 minutes). Supernatants are removed, and pellets are resuspended in 100 µl of buffer. The pellets and supernatants can be brought up to 300 µl (e.g., with BRB80), and the relative fluorescence signals in the supernatant and the pellet are quantitated using a Perkin Elmer L25B luminescence spectrometer.

E) Liquid Crystal Assay Systems

In still another embodiment, binding of the microtubule depolymerizing or severing proteins to microtubules can be detected by the use of liquid crystals. Alternatively, it is expected that liquid crystals can be used to monitor the state of tubulin polymerization.

Liquid crystals can be used to amplify and transduce receptor-mediated binding of proteins at surfaces into optical outputs. Spontaneously organized surfaces can be designed so that protein molecules, upon binding to ligands (e.g., microtubules) hosted on these surfaces, trigger changes in the orientations of 1- to 20-micrometer-thick films of supported liquid crystals, thus corresponding to a reorientation of ~$10^5$ to $10^6$ mesogens per protein. Binding-induced changes in the intensity of light transmitted through the liquid crystal are easily seen with the naked eye and can be further amplified by using surfaces designed so that protein-ligand recognition causes twisted nematic liquid crystals to untwist (See, e.g., Gupta et al. (1998) *Science,* 279: 2077–2080). This approach to the detection of ligand-receptor binding does not require labeling of the analyte, does not require the use of electroanalytical apparatus, provides a spatial resolution of micrometers, and is sufficiently simple that it is useful in biochemical assays and imaging of spatially resolved chemical libraries.

D) Synthesis or Expression of Microtubule Depolymerizing or Severing Proteins i) De novo Chemical Synthesis Using the information provided, herein, the microtubule depolymerizing or severing proteins, protein subunits, or subsequences thereof may be synthesized using standard chemical peptide synthesis techniques. Where the desired subsequences are relatively short, the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology.* VOL 2: *Special Methods in Peptide Synthesis, Part A.;* Merrifield, et al. (1963) *J. Am. Chem. Soc.,* 85: 2149–2156; and Stewart et al. (1984) *Solid Phase Peptide Synthesis,* 2nd ed. Pierce Chem. Co., Rockford, Ill.

ii) Recombinant Expression

In a preferred embodiment, the microtubule depolymerizing or severing proteins, protein subunits, or subsequences, are synthesized using recombinant DNA methodology. Generally this involves creating a DNA sequence that encodes the protein, placing the DNA in an expression cassette under the control of a particular promoter, expressing the protein in a host, isolating the expressed protein and, if required, renaturing the protein. DNA encoding the microtubule depolymerizing or severing proteins, protein subunits, or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, the microtubule depolymerizing or severing proteins, of this invention can be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired the microtubule depolymerizing or severing protein having terminal restriction sites. This nucleic acid can then be easily ligated into a vector containing a nucleic acid encoding the second molecule and having the appropriate corresponding restriction sites.

Suitable PCR primers can be determined by one of skill in the art using the sequence information provided herein. Appropriate restriction sites can also be added to the nucleic acid encoding the microtubule depolymerizing or severing proteins by site-directed mutagenesis. The plasmid containing the microtubule depolymerizing or severing protein encoding nucleic acid is cleaved with the appropriate restriction endonuclease and then ligated into the vector encoding the second molecule according to standard methods.

The nucleic acid sequences encoding the microtubule depolymerizing or severing proteins may be expressed in a variety of host cells, including *E. Coli,* other bacterial hosts, yeast, and various higher eukaryotic cells such as the COS, CHO and HeLa cells lines and myeloma cell lines. As the microtubule depolymerizing or severing proteins are typically found in eukaryotes, a eukaryote host is preferred. The recombinant protein gene will be operably linked to appropriate expression control sequences for each host. For *E. coli,* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant the microtubule depolymerizing or severing proteins can be purified according to standard procedures of the art, including ammonium sulfate precipitation, affinity columns, column chromatography, gel electrophoresis and the like (See generally, R. Scopes, (1982) *Protein Purification,* Springer-Verlag, N.Y.; Deutscher (1990) *Methods in Enzymology Vol.* 182: *Guide to Protein Purification.,* Academic Press, Inc. N.Y.). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill in the art would recognize that after chemical synthesis, biological expression, or purification, the microtubule depolymerizing or severing protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.,* 268: 14065–14070; Kreitman and Pastan (1993) *Bioconjug. Chem.,* 4: 581–585; and Buchner, et al., (1992) *Anal. Biochem.,* 205: 263–270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the microtubule depolymerizing or severing proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., polyHis) placed on either terminus to create conveniently located restriction sites or termination codons or purification sequences.

In a particularly preferred embodiment, the katanin protein(s) are expressed as described in Example 1, while XKCM1 is expressed and purified as described by Walczak et al (1996) supra.

V. Data Management

In one embodiment, the assays of this invention are facilitated by the use of databases to record assay results. Particular with the use of large-scale screening systems, (e.g., screening of combinatorial libraries) data management can become a significant issue. For example, all natural hexapeptides have been synthesized in a single combinatorial experiment producing about 64 million different molecules. Maintenance and management of even a small fraction of the information obtained by screening such a library is aided by methods automated information retrieval (e.g., a computer database).

Such a database is useful for a variety of functions, including, but not limited to library registration, library or result display, library and/or result specification, documentation, and data retrieval and exploratory data analysis. The registration function of a database provides recordation/registration of combinatorial mixtures and assay results to protect proprietary information in a manner analogous to the registration/protection of tangible proprietary substances. Library and assay result display functions provide an effective means to review and/or categorize relevant assay data. Where the assays utilize complex combinatorial mixtures for test agents, the database is useful for library specification/description. The database also provides documentation of assay results and the ability to rapidly retrieve, correlate (or conduct other statistical analysis), and evaluate assay data.

Thus, in some preferred embodiments, the assays of this invention additionally involve entering test agent(s) identified as positive (i.e., having an effect on microtubule polymerization, and/or depolymerization, and/or severing) in a database of "positive" compounds and more preferably in a database of therapeutic or bioagricultural lead compounds.

The database can be any medium convenient for recording and retrieving information generated by the assays of this invention. Such databases include, but are not limited to manual recordation and indexing systems (e.g., file-card indexing systems). However, the databases are most useful when the data therein can be easily and rapidly retrieved and manipulated (e.g., sorted, classified, analyzed, and/or otherwise organized). Thus, in a preferred embodiment, the signature the databases of this invention are most preferably "automated" (e.g., electronic [e.g., computer-based]) databases. The databas e can be present on an individual "stand-alone" computer system, or a component of or distributed across multiple "nodes" processors) on a distributed computer systems. Computer systems for use in storage and manipulation of databases are well known to those of skill in the art and include, but are not limited to "personal computer systems," mainframe systems, distributed nodes on an inter- or intra-net, data or databases stored in specialized hardware (e.g., in microchips), and the like.

VI. Kits for Screening for Modulators of Microtubule Depolymerization or Microtubule Severing Agents In still another embodiment, this invention provides kits for the practice of any of the methods described herein. The kits comprise one or more containers containing one o r more of the assay components described herein. Such components include, but are not limited to stabilized microtubules, microtubule depolymerizing or microtubule severing proteins or protein subunits, one or more test agents, reaction media, solid supports (e.g., microtitre plates) with attached components, buffers, labels, and other reagents as described herein.

The kits may optionally include instructional materials containing directions (i.e., protocols) for carrying out any of the assays described herein. While the instructional materials typically comprise written or printed materials they are not limited to such. Any medium capable of storing such instructions and communicating them to a n e nd user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Katanin, a Microtubule-severing Protein is a Novel AAA ATPase that Targets to the Centrosome Using a WD40-containing Subunit

RESULTS

To begin dissecting the functional domains of katanin, we isolated cDNA clones for the p60 and p80 subunits from cDNA derived from sea urchin (*Strongylocentrotus purpuratus*) egg mRNA. After first obtaining peptide sequence of several proteolytic fragments from the two sea urchin katanin subunits, cDNA clones were isolated using a combination of degenerate PCR, cDNA library screening, and anchor-ligated PCR (see Experimental Procedures). The predicted amino acid sequences of the cDNA clones contained 139 amino acids (a.a.) and 306 amino acids of peptide sequences obtained by direct microsequencing of p60 and p80 respectively.

60 is Novel Member of the AAA ATPase Superfamily

Sequence analysis of the p60 cDNA clone revealed an open reading frame that encodes a 516 a.a. polypeptide (FIG. 1A). A BLAST search with the predicted p60 protein sequence revealed that this polypeptide contains a C-terminal domain (a.a. 231–447) that is highly conserved in the AAA ATPase Superfamily (FIG. 1B) (Confalonieri et al. (1995) *BioEssays* 17: 639–650). This ~220 amino acid region contains the "Walker A" (P-loop) and "Walker B" motifs found in many ATPases (Walker et al (1982) *EMBO J.* 1: 945–95 1). AAA proteins, which contain either one or two of these 220 a.a. ATP-binding modules, constitute a large superfamily whose members have been implicated in a variety of cellular functions (Confalonieri et al. (1995) supra.).

Of the AAA domains entered into sequence data bases, mei-1, a *C. elegans* protein required for meiosis (Clark-Maguire et al. (1994) *Genetics* 13 6: 533–546), is most closely related to p60 (55% a.a. identify, FIG. 1B). Mei-1 was discovered in a genetic screen as a protein that is required for meiotic spindle formation, but disappears during subsequent mitotic divisions. Interestingly, both p60 (McNally et al. (1996) *J. Cell Sci.* 109: 561–567) and mei-1 (Clark-Maguire et al. (1994) *J. Cell Biol.* 126: 199–209) are localized to spindle poles in a microtubule-dependent manner. However, the N-terminal half of p60 has no significant homology to mei-1, suggesting that p60 and mei-1 may not be orthologs. BLAST searches with p60 sequences, however, revealed several human ESTs (expressed sequence tags) that have strong amino acid identity outside of the AAA domain, suggesting the existence of vertebrate homologs of p60.

p80 Contains WD40 Repeats

Sequence analysis of the sea urchin p80 cDNA clone revealed a predicted 690 a.a. polypeptide that contains six "WD40" repeat motifs extending from residues 1–256 (FIG. 2A). An alignment of these repeats with two unrelated WD40 repeat-containing proteins is shown in FIG. 2B. The WD40 repeats in several proteins have been documented to participate in protein-protein binding interactions (Komachi et al. (1994) *Genes Dev.* 8: 2857–2867; Wall et al. (1995) *Cell* 83: 1047–1058). The C-terminal region of p80 (residues 257–690) did not exhibit significant amino acid identity to any previously described protein. However, significant identity of sea urchin p80 was observed with several human EST clones. The sequences of these clones were used to isolate a full length human p80 katanin homolog by PCR (see Experimental Procedures). The human cDNA encodes a predicted 655 a.a. protein with 61% a.a. identity in the WD40 domain (a.a. 1–256) (FIG. 2B), 23% a.a. identity in the central 187 residues, and 54% a.a. identity in the C-terminal 164 a.a. with *S. purpuratus* p80 katanin (latter two regions are not shown).

Baculovirus Expression and Molecular Structure of the Katanin Subunits

Figure 3B:
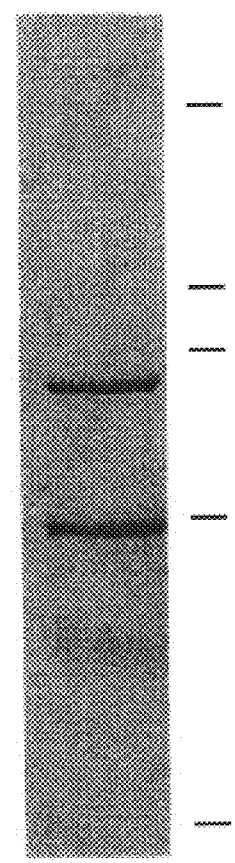

Deciphering the roles of the two katanin subunits is essential for understanding the enzyme's mechanism and biological activities. However, separation of the native sea urchin p60/p80 subunits requires denaturing conditions. We therefore sought to express the two subunits together and separately and then test their enzymatic activities. Bacterial expression of p60 produced largely insoluble protein, and the small amount of soluble p60 had no microtubule-stimulated ATPase activity (data not shown). However, using the baculovirus expression system, we obtained soluble p60, p80, and the p60/p80 complex (each expressed with a N-terminal His$_{(6)}$ tag SEQ ID NO:14), and purified the expressed proteins using metal affinity chromatography (FIG. 3A). When p60 and p80 were co-expressed, the stoichiometry of the two subunits in the purified protein was approximately equal (1.0:0.9 p60:p80 molar ratio, as determined by Coomassie staining). Moreover, immunoprecipitation with an anti-p60 antibody led to co-immunoprecipitation of equal quantities of p60 and p80 (FIG. 3B). These results indicate that baculovirus -expressed p60 and p80 heterodimerize, as observed with native katanin McNally and Vale (1993) *Cell,* 75: 419–429).

Figure 4A:
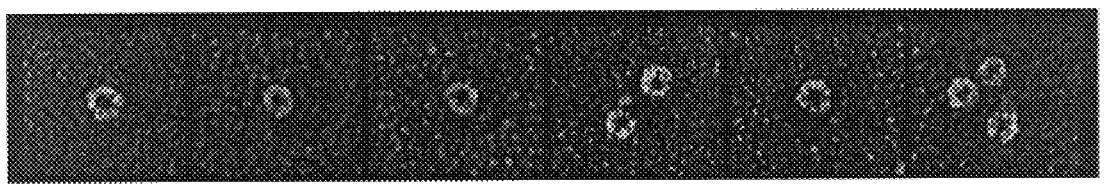
FIG. 4 shows the structure of katanin as visualized by rotary-shadowing electron microscopy. Panel A shows 14–16 nm diameter rings observed in preparations of recombinant p60. Panel B shows single particles of recombinant p80; occasional aggregates are seen (rightmost picture) but rings are never observed. Panels C and D show different rings observed in recombinant p60/p80 preparations. Panel C shows a "splayed" complex, consisting of a central p60-like ring surrounded by a halo particles that resemble p80. In Panel D, intact 20 nm diameter rings are seen with bright edges, suggesting they extend >10 nm above the mica surface. All images are shown at 300,000×. The dimensions indicated above include the platinum shadowing, which typically adds 2 nm of material to the protein surface.
Figure 4B:
Figure 4C:
Figure 4D:
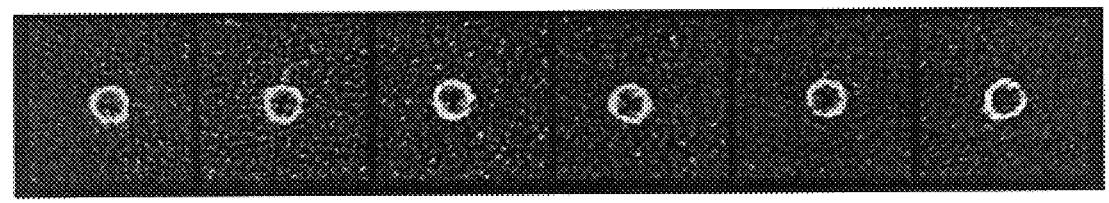

To examine katanin's structure, baculovirus-expressed p60, p80, or p60/80 was adsorbed onto mica chips, and the chips were subsequently frozen, etched, and rotary shadowed with platinum (Heuser (1989) *J. Electron Microsc. Technique* 13:, 244–263; Heuser (1983) *J. Mol. Biol.* 169:155–195). The platinum-shadowed p60 appeared as a 14–16 nm ring punctuated in the center by a 3–5 nm opening, often with what appears to be cracks radiating outward (FIG. 4A). p80, on the other hand, appeared as ~11 nm particles and occasional unstructured protein aggregates; rings were not observed (FIG. 4B). Rings were also seen for p60/p80 complexes (FIGS. 4C, 4D) and native sea urchin katanin (data not shown). Interestingly, two types of p60/p80 complexes were visible: large ~20 nm diameter rings with bright edges, which is suggestive of taller complexes that extend upward from the mica (FIG. 4D), and smaller rings of the size of p60 alone with several p80 sized particles radiating from the central ring (FIG. 4C). The large and small rings might represent closed and "splayed" versions of the p60/p80 complex, respectively, which could be produced if the complex dissociates upon mica adsorption. Both p60 and p60/p80 structures resemble the rings observed for the AAA ATPases NSF and p97, whose dimensions are 15–17 nm (Hanson et al. (1997) *Cell* 90: 523–535).

p60 Katanin has Microtubule-Stimulated ATPase and Severing Activity

Figure 5A:
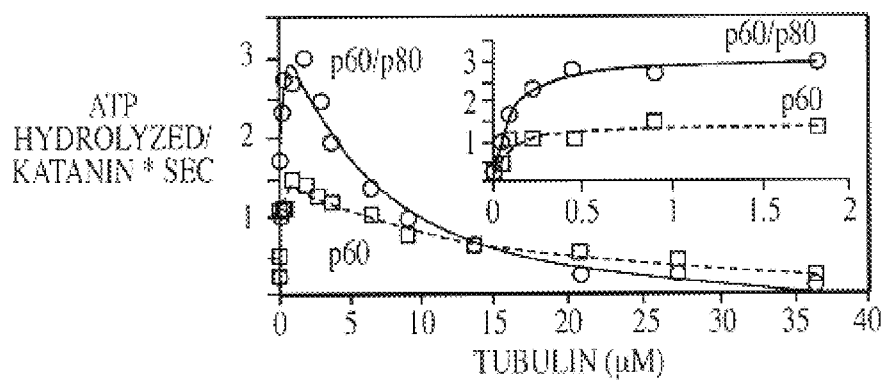
FIGS. 5A, 5B, and 5C illustrate the activities of recombinant katanin subunits.

With the availability of isolated p60 and p80, we then examined whether the individual subunits have ATPase activity. The co-expressed p60/p80 heterodimer displayed an ATP turnover rate of 0.3 ATP/sec/heterodimer; this activity was stimulated ~10-fold by microtubules (FIG. 5A). This basal activity and the fold stimulation by microtubules are similar to that observed for native sea urchin katanin (data not shown). Consistent with the finding of an AAA domain in its sequence, p60 alone displayed a microtubule-stimulated ATPase activity. Surprisingly, the maximal basal and microtubule-stimulated ATPase rates of p60 were only 2-fold lower than those of the p60/p80 heterodimer (FIG. 5A). p80 itself had no detectable ATPase activity. The activation of ATPase activity by microtubules displayed an atypical, non-hyperbolic behavior. ATP turnover by p60 and p60/p80 was stimulated at low concentrations of microtubules (peak at ~2 $\mu$M tubulin), but then decreased at higher microtubule concentrations (FIG. 5A). This same complex pattern of microtubule stimulation was also observed for native sea urchin katanin (data not shown).

Figure 5B:
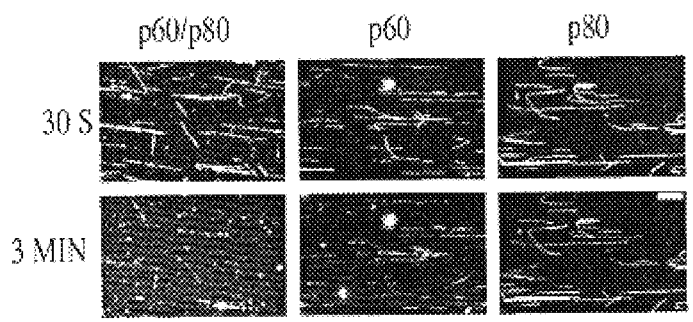

We then tested the microtubule severing activity of p60, p80, and p60/p80 using a fluorescence microscopy assay (McNally and Vale (1993) Cell, 75: 419–429). Both p60 and p60/p80 severed microtubules in this assay (FIG. 5B). Broken microtubules were observed within 1 min after introducing 0.1 $\mu$M p60 or p60/p80, and microtubules were completely disassembled after 5 min. The reaction appeared somewhat slower with p60 alone. Microtubules remained intact if ATP was omitted from the reaction (not shown). In contrast, p80 was unable to sever microtubules at concentrations 5-fold higher than those used for p60 (FIG. 5B). These experiments demonstrate that p60 alone can carry out all of the steps necessary for coupling ATP hydrolysis to microtubule disassembly.

Figure 5C:
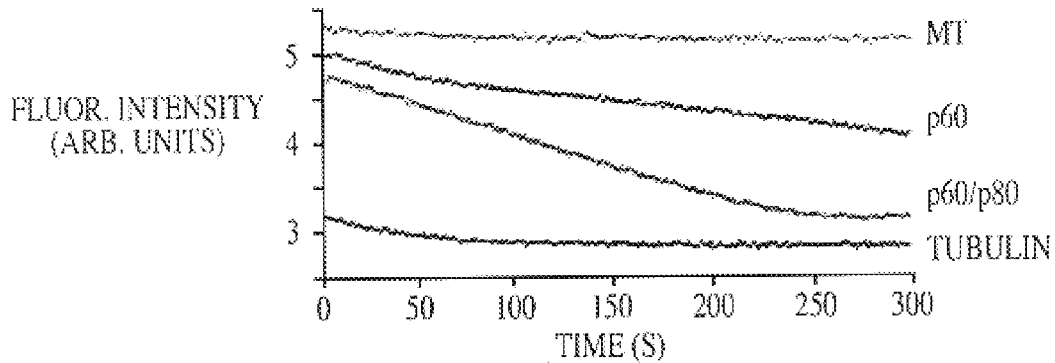

To better compare the microtubule severing activities of p60 and p60/p80, we developed a quantitative microtubule disassembly assay based upon a previous finding that DAPI fluorescence intensity is higher when this dye is bound to polymerized versus free tubulin (Heusele et al. (1987) Eur. J Biochem. 165: 613–620). When katanin and ATP were incubated with DAPI-labeled microtubules, a linear decrease in fluorescence intensity was observed as a function of time, reflecting the conversion of microtubules to tubulin (FIG. 5C. The loss of microtubule polymer was confirmed by centrifugation studies, which showed an increase in non-sedimentable tubulin with a similar time course (data not shown). The fluorescence decrease induced by these enzymes reached a steady-state level that was slightly higher than pure, monomeric tubulin, suggesting that some tubulin oligomer may exist at steady state. The rate of fluorescence decrease was proportional to p60 or p60/p80 concentration over a 10-fold range (data not shown). When the rates of microtubule disassembly were compared, p60 was half as active as p60/p80 (FIG. 5C). This slower rate of microtubule disassembly is consistent with the previously described 2-fold decrease in ATPase activity of p60 compared with p60/p80.

The p80 WD40 Domain Targets to the Centrosome

The finding that p60 by itself can sever microtubules left open the question of the function of the p80 katanin subunit. At least two functional domains of p80 could be postulated. First, since katanin is a heterodimer (McNally and Vale (1993) Cell, 75: 419–429), some part of p80 must be involved in heterodimerization with p60. Second, because previous studies have shown that katanin is concentrated at centrosomes in vivo (McNally et al. (1996) J Cell Sci. 109: 561–567), p80 could contain a domain that interacts with a centrosomal protein to allow targeting of the katanin holoenzyme. Because WD40 repeats have been implicated in heterophilic protein-protein interactions (Komachi et al. (1994) Genes Dev. 8: 2857–2867; and Wall et al. (1995) Cell 833: 10471058), the six WD40 repeats in p80 represented a good candidate domain for participating in either dimerization or centrosome targeting.

Figure 6:
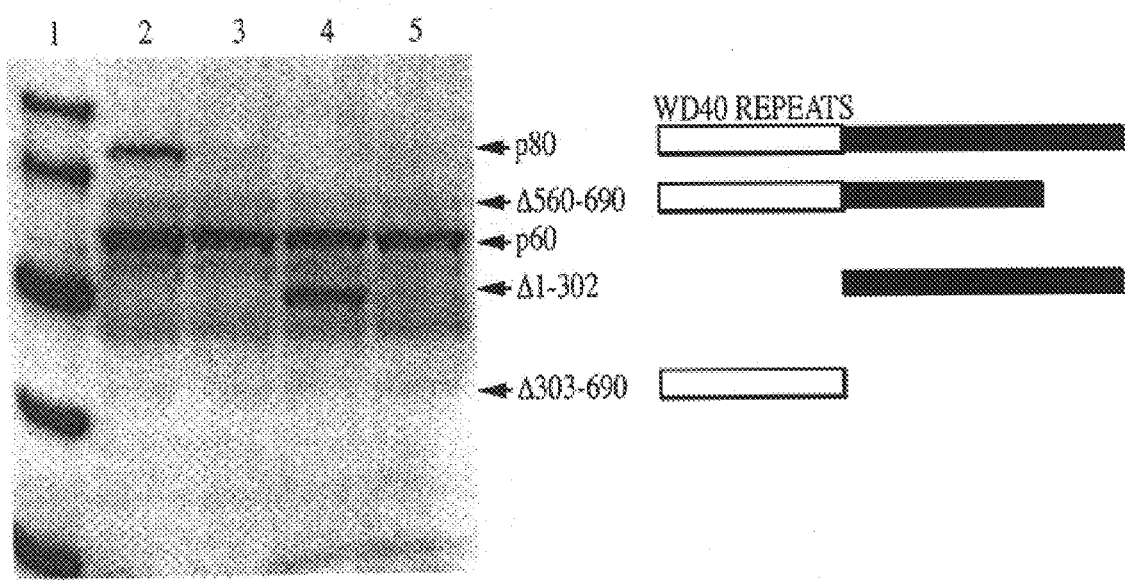
FIG. 6 shows that the WD40 repeats of p80 katanin are not required for interaction with p60 katanin. Epitope-tagged derivatives of p80 and p60 were synthesized in vitro in a combined transcription-translation reaction. p60 and interacting proteins were immunoprecipitated with a p60-specific antibody and the resulting immunoprecipitates were resolved by SDS-PAGE and blotted to nitrocellulose. In vitro translated proteins were detected by chemiluminescence as described in Experimental Procedures. Lane 1: molecular weight standards Mr: 100,000, 75,000, 50,000, 35,000 and 25,000; lane 2: p60 co-translated with full-length p80; lane 3: p60 co-translated with the Δ560–690 derivative of p80; lane 4: p60 co-translated with the Δ1–302 derivative of p80; lane 5: p60 co-translated with the Δ303–690 derivative of p80. The structure of each deletion derivative of p80 is shown at right. The Δ560–690 and Δ303–690 translation products were detected in the supernatants of the immunoprecipitations (not shown).
Figure 7A:
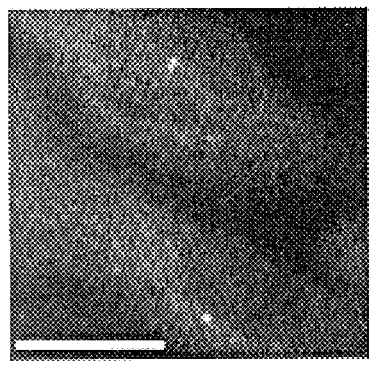
FIG. 7 shows that human p80 katanin and a fusion protein of the human p80 WD40 domain with GFP co-localize with γ-tubulin at centrosomes of MSU1.1 human fibroblasts. Panels A and B: Co-localization of immunofluorescence staining by a human p80 katanin-specific antibody (Panel A) and a γ-tubulin specific antibody (Panel B). Panels C–F show co-localization of GFP fluorescence (Panels C and E) with staining by a γ-tubulin-specific antibody (Panels D and F). Co-localization to two centrosomes seen in Panel C and Panel D while co-localization to a single centrosome is seen in Panels E and F. The apparently higher background of cytoplasmic green fluorescence in Panel E relative to Panel C is a display artifact. The fluorescence intensity of the centrosomes in Panel C is at least 5 fold greater than that of the centrosome in Panel E. The p80 antibody was detected with an Oregon Green 488 second antibody and the γ-tubulin antibody was detected with a Texas Red-X second antibody. Fluorescence signals were separated with fluorescein and Texas Red filter sets (Chroma Technologies). Bar=14 µm.
Figure 7B:
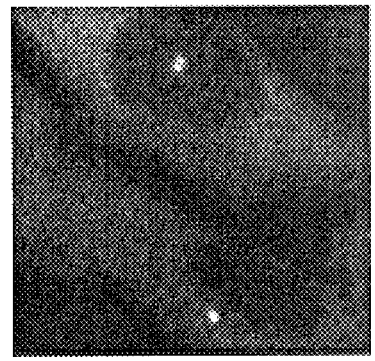
Figure 7C:
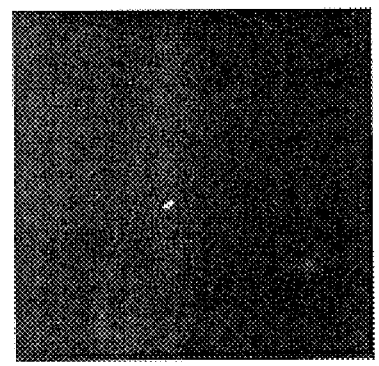
Figure 7D:
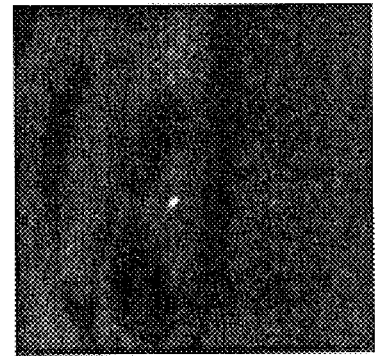
Figure 7E:
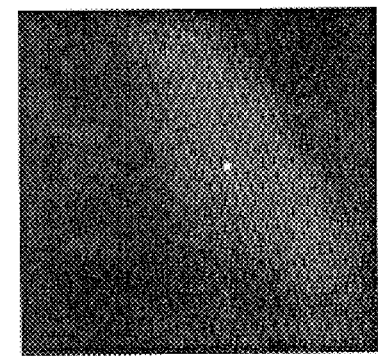
Figure 7F:
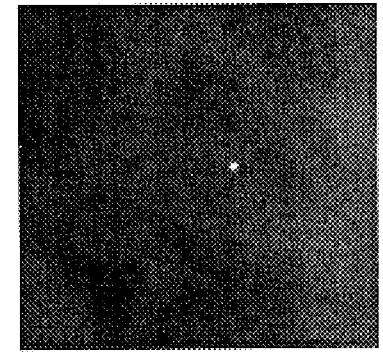

In order to test whether the WD40 repeats of p80 are required for heterodimerization with p60, we deleted the entire WD40 domain and examined whether the truncated p80 (p80Δ1–302) interacted with p60 when the two polypeptides were co-translated in a rabbit reticulocyte system. The truncated p80 (p80Δ1–302) was co-immunoprecipitated by the anti-p60 antibody only in the presence of p60 and just as efficiently as full length p80 (FIG. 6). This finding indicates that the WD40 repeats are not required for dimerizing the two katanin subunits. Nevertheless, it remained possible that the WD40 domain was one of multiple, redundant p60-interacting domains. However, a C-terminal truncation of p80 (p80Δ3 03–690) containing only the WD40 domain did not coimmunoprecipitate with p60 (FIG. 6). These results indicate that the p80 WD40 repeats are neither necessary nor sufficient for dimerization with p60. To determine which region of p80 is required for interaction with p60, a p80 deletion lacking the C-terminal 130 amino acids (p80Δ560–690) was constructed and was found not to co-immunoprecipitate with p60 (FIG. 6). These findings suggest that the C-terminal 130 amino acids of p80, but not the WD40 repeat domain, are involved in the dimerization with p60.

To examine whether the p80 WD40 repeats bind to a protein in the centrosome, we tested whether these repeats can target a heterologous protein (green fluorescent protein, GFP) to the centrosome after transient transfection in the human fibroblast cell line, MSU1.1 (Lin et al. (1995) Int. J. Cancer 63: 140–147). The WD40 domain of human p80 katanin was used, because it was more likely that the human protein would interact with centrosomal proteins in this human cell line. Immunofluorescence of MSU1.1 cells with an antibody specific for human p80 katanin (see Experimental Procedures) showed labeling of the cytoplasm and more concentrated staining at one or two spots that co-localized with $\gamma$-tubulin staining (FIG. 7), confirming that endogenous katanin is concentrated at centrosomes in fibroblasts as it is in sea urchin embryos (McNally et al. (1996) J Cell Sci. 109: 561–567). In contrast to the localization in sea urchin embryos, the concentration of p80 at centrosomes in fibroblasts remained after complete depolymerization of microtubules with nocodazole (data not shown), suggesting that katanin is bound to the pericentriolar material. When a fusion protein consisting of the six WD40 repeats of human p80 katanin (a.a. 1–263) appended to the N-terminus of green fluorescent protein (GFP) was expressed in MSU1.1 cells, one or two foci of green fluorescence that co-localized with $\gamma$-tubulin staining was observed 2–4 hr after transfection in addition to diffuse cytoplasmic fluorescence (FIG. 7). Identical results were obtained in transfections of HeLa cells (not shown). In contrast to these findings, cells transfected with GFP alone never revealed foci of green fluorescence at centrosomes (not shown). After longer periods of expression (8–24 hr) of p80 WD40-GFP, numerous heterogeneously-sized bright foci of green fluorescence appeared that did not co-localize with $\gamma$-tubulin, and later, massive aggregates several $\mu$m in diameter were observed (not shown). These results indicate that the WD40 repeats of human p80 katanin are sufficient to target GFP to the centrosome and suggest that once the centrosome binding sites are saturated, the additional fusion protein aggregates in the cytoplasm.

Discussion

Katanin is a unique enzyme that couples ATP hydrolysis to the dissociation of tubulin subunits from the microtubule lattice (McNally and Vale (1993) Cell, 75: 419–429). Other than the motor proteins kinesin and dynein, katanin is the only known microtubule-associated ATPase. In this study, we have determined the primary structure of the p60 and p80 katanin subunits and examined the roles of the two subunits in microtubule severing and the cellular localization of the enzyme.

Mechanism of Katanin-Mediated Microtubule Severing

Sequence analysis of p60 katanin revealed that it is a novel member of the AAA family of ATPases. This finding suggested that p60 might be responsible for the previously reported ATPase activity of the native katanin dimer (McNally and Vale (1993) Cell, 75: 419–429). However, neither p60 nor p80 contained an identifiable microtubule binding sequence, such as those found in tau (Butner and Kirschner (1991) J. Cell Biol., 115: 717–730) or MAP1B (Noble et al. (1989) J. Cell Blol. 109: 3367–3376), and therefore it was not possible to ascribe the microtubule binding and severing activities of katanin to either subunit based upon sequence information alone. By measuring the activities of the p60 and p80 subunits purified individually and together as a dimer, we have found that katanin's p60 subunit exhibits both microtubule-stimulated ATPase activity and microtubule-severing activity in the absence of the p80 subunit. Since p60 has all elements required for functional interactions with microtubules, future structure-function studies on the mechanism of microtubule severing can be focused on this single subunit. Furthermore, we have found that p60 katanin can form rings, the dimensions and appearance of which are similar to those reported for the AAA proteins NSF and p97 (Hanson et al. (1997) Cell 90: 523–535). The comparison of p60 with other AAA proteins provides clues as to how katanin disassembles microtubules, as discussed below.

The ATPase properties of katanin show both similarities and differences with other AAA family members. Katanin's basal ATPase activity of 0.3 ATP/katanin/sec and maximal microtubule-stimulated rate of 3 ATP/katanin/sec are comparable to values of 1 ATP/sec for p97 (Peters et al. (1992) J. Mol. Biol., 223: 557–571) and 0.08 ATP/sec for recombinant NSF (Morgan et al. (1994) J. Biol. Chem. 269: 29347–29350). NSF ATPase is also stimulated two-fold upon binding to its target protein, α- or γ-SNAP (Morgan et al. (1994) J. Biol. Chem. 269: 29347–293 50). However, katanin's ATPase activity displays a complex stimulation by microtubules. At low microtubule concentrations (<2 μM), ATPase activity increases with increasing microtubule concentration, but at higher microtubule concentrations, ATPase activity decreases until it eventually approaches basal levels. In contrast, stimulation of kinesin ATPase by microtubules (Gilbert et al. (1993) Biochemistry 32: 4677–4684) displays typical hyperbolic curves that reach saturation.

At least two potential explanations could account for the unusual ATPase behavior of katanin. One possibility is that katanin binds microtubules at two sites, which could elevate the local microtubule concentration by crosslinking and thereby stimulate katanin's ATPase activity. At higher microtubule concentrations, however, the ratio of katanin to microtubules would be lower, resulting in a less-crosslinked network and less stimulation of ATPase activity. In support of this idea, bundling of microtubules by katanin has been observed by microscopy (unpublished observations). This behavior has been seen in another cytoskeletal-polymer stimulated ATPase, Acanthamoeba myosin 1, which has two discrete actin binding sites: a low affinity catalytic site and a higher affinity site not involved in catalysis (Lynch et al. (1986) J. Biol. Chem. 261: 17156–17162).

A second explanation for katanin's complex enzymatic behavior could involve katanin oligomerization into rings. Rotary-shadowing EM images show oligomeric ring structures in katanin preparations; however hydrodynamic experiments with both native (McNally and Vale (1993) Cell, 75: 419–429) and recombinant katanin (data not shown) suggest that the majority of the protein is monomeric. One hypothesis is that microtubules promote p60—p60 oligomerization, and that the assembly of p60 monomers into a higher order structure on the microtubule stimulates ATPase activity. According to this idea, low microtubule concentrations would facilitate multimerization, since p60 monomers would be more likely to bind near one another on the microtubule. High microtubule concentrations, on the other hand, would inhibit p60 assembly by sequestering p60 monomers at noncontiguous sites on the lattice. Self assembly into rings also has been suggested as the cause of dynamin's biphasic stimulation of GTPase activity (Tuma and Collins (1994) J. Biol. Chem. 269: 30842–30847; and Warnock et al. (1996) J. Biol. Chem. 271: 22310–22314). Cryo-electron microscopy studies of the p60-microtubule complex provide a means of testing this hypothesis.

Based upon studies of other AAA family members, katanin oligomers/rings may prove to be important in the severing mechanism. Although serving diverse functions, many AAA proteins appear to share a common function as nucleotide-dependent molecular chaperones that disassemble protein complexes (Confalonieri and Duguet (1995) supra.). The best studied AAA member is NSF, which binds to and induces the disassembly of ternary SNARE complexes after hydrolysis of ATP (Hanson et al. (1995) J. Biol. Chem. 270: 1695 5–16961; and Hayashi et al. (1995) EMBO J 14: 2317–2325). This reaction plays a role either in vesicle fusion and/or recycling of components in membrane trafficking pathways. Recently, electron microscopy studies have revealed that the NSF ring structure adopts extended and compact conformations in the ATP-γ-S and ADP states, respectively (Hanson et al, (1997) Cell 90: 523–535). If attached at several points to a protein complex, this transition could break apart bonds in the SNARE complex (Hanson et al., (1997) supra.). Katanin may work in an analogous fashion. A ring of katanin's dimensions could potentially contact multiple tubulin sites on a microtubule, and a structural change during ATP hydrolysis could shift the positions of tubulin binding sites with respect to one another, which would disrupt the microtubule lattice. Another possibility is that katanin acts more like an ATP-regulated version of actin severing proteins, which are thought to compete for sites at protein-protein interfaces within the polymer. In this type of mechanism, the AAA domain could serve as an ATP-dependent protein clamp that binds tightly to and disrupts tubulin-tubulin interfaces during particular steps in the ATPase cycle.

Targeting of Katanin to Centrosomes

Our studies show that p80 does not constitute an essential element of katanin's enzymatic mechanism. The finding that p80 is not required for microtubule-severing activity was somewhat surprising, because all of the p60 immunoprecipitates with p80 from sea urchin cytosol (unpublished observations). However, experiments reported here have uncovered a role for p80 in targeting katanin to centrosomes in vivo. This conclusion is based upon the finding that the WD40 domain of p80 can target GFP to the centrosome in cultured human cell lines. Because the WD40 domain cannot dimerize with endogenous p60, the centrosomal localization must be due to direct interaction of the WD40 domain with one or more resident centrosomal proteins. WD40 domains are thought to form a conserved beta propeller structure, as first determined for the beta subunits of transducin and $G_i$ (Wall et al. (1995) Cell 83: 1047–1058; Sondek et al. (1996) Nature 379: 369–374). However, each WD40 domain exhibits very specific heterophilic protein interactions; exposed residues in the beta subunit of $G_i$ interact with the alpha subunit (Wall et al. (1995) supra.), whereas the corresponding residues in the WD40 transcription factor TUP1 mediate binding to a second transcription factor α2 (Komachi, and Johnson (1997) Mol. Cell Biol. 17: 6023–6028). Since the G protein beta subunits interact with multiple partner proteins (Wall et al. (1995) Cell 83: 1047–1058; and Gaudet et al. (1996) Cell, 87: 577–588), it is also possible that the p80 katanin WD40 domain can interact with more than one protein in vivo. p80 is the only known centrosomal protein with a WD40 motif. The findings that katanin has an entire subunit devoted to centrosome localization and that this subunit is conserved between mammals and echinoderms suggest an important role for katanin at the centrosome.

The WD40 domain of p80 katanin represents the first example of a structural motif that targets a protein to the centrosome in mammals, although a centrosome-targeting domain has been defined for the Drosophila protein CP190 (Oegema et al. (1995) J. Cell Biol. 131: 1261–1273). This provides an opportunity to identify the centrosomal component(s) responsible for anchoring katanin. Further information on the docking of katanin to the centrosome may provide clues regarding katanin's role in microtubule disassembly at this organelle.

Experimental Procedures

Peptide Microsequencing

Katanin was purified from extracts of S. purpuratus eggs essentially as described previously (McNally and Vale (1993) Cell, 75: 419–429), except that the hydroxyapatite chromatography was carried out using a Pharmacia HRI. 0/3 0 column packed with 20 μm, ceramic hydroxyapatite beads (American International Chemical, Natick, Mass.). Internal peptide sequences of the p60 and p80 subunits were obtained from native sea urchin katanin as described (Iwamatsu (1992) Electrophoresis 13: 142–147). Two additional p80 peptides were also obtained: DASMMAM (SEQ ID NO:15) and IQGLR (SEQ ID NO:16).

p60 Cloning

A cDNA encoding a 400 bp fragment of the p60 subunit (corresponding to a.a. 214374) was cloned from S. purpuratus first strand cDNA using nested PCR with degenerate oligonucleotides. This fragment was then used to screen a lambda ZAP-Express cDNA library made from S. purpuratus unfertilized egg mRNA by hybridization. Several independent positive clones were isolated. One clone was completely sequenced (GENBANK accession #AF052191).

p80 Cloning

An initial partial cDNA clone of p80 katanin was obtained by screening an S. purpuratus unfertilized egg cDNA library (Wright et al. (1991) J. Cell Biol. 113: 817–833) with an antibody specific for p80 katanin, anti-p81$^{aff}$ (McNally et al. (1996) J. Cell Sci. 109: 561–567). The insert of the initial clone was used to isolate a longer cDNA clone (pFM18) from the same library by plaque hybridization. A cDNA clone encoding the 5' end of p80 katanin (pFM23) was obtained by anchor-ligated PCR (Apte and Siebert (1993) Biotechniques 15: 890–893) using primers derived from pFM18 sequences and reverse transcription reactions utilizing S. purpuratus unfertilized egg mRNA as template. A full-length p80 cDNA (GENBANK accession #AF052433) was generated by joining the inserts of pFM1 and pFM23 at a common BstXI site.

BLAST searches of GENBANK with p80 sequences revealed homology with a human infant brain cDNA (GENBANK accession #T 16102) which was obtained and sequenced. Sequences obtained from the T 16102 clone were used to obtain multiple 3' end cDNA clones by 3' RACE from HT1080 (human fibrosarcoma) total RNA. An overlapping cDNA clone (pFM54) containing the translation start site was obtained by PCR amplification from an adult human hippocampal cDNA library (Stratagene, Inc.). Sequence analysis of partial cDNAs PCR amplified from HT1080 total RNA or from the hippocampal library were over 98% identical in predicted a.a. sequence. The complete DNA sequence of human p80 katanin is available from GENBANK (accession #AF052432).

Antibody Production and Immunoprecipitation

The full-length S. purpuratus p60 cDNA coding sequence was inserted into pMALC2 (New England Biolabs) and expressed as a C-terminal fusion to maltose binding protein in E. coli. Soluble MBP-p60 fusion protein was purified on an amylose affinity column, eluted with maltose, and injected into rabbits (antiserum production by BABCO, Berkeley, Calif.). To select p60-specific antibodies that do not react with other AAA members, antibodies recognizing the N-terminal non-AAA domain of p60 were affinity purified on an Affi-Gel column coupled with the N-terminal residues 1- 152 of p60 fused to MBP (Harlow and Lane (1988). Antibodies: A Laboratory Manual. (Cold Spring Harbor, N.Y.: Cold Spring Harbor Laboratory Press)). The resulting affinity-purified antibody recognized a single 60 kDa polypeptide in immunoblots of S. purpuratus unfertilized egg extract.

To prepare a specific antibody to human p80 katanin, the full length human p80 cDNA was ligated into the E. coli expression vector, pET-28a$^+$ (Novagen) as a BamHI-XhoI fragment. The protein was expressed and then purified in a denatured state in 8 M urea by nickel chelate chromatography on His-Bind Resin (Novagen). Rabbits were immunized with polyacrylamide slices containing SDS-PAGE resolved human p80 katanin. Resulting serum was affinity purified with CNBr Sepharose-coupled, bacterially-expressed human p80 katanin. The resulting affinity purified antibody recognized a single 80 kDa polypeptide in immunoblots of SDS solubilized HeLa cells (not shown).

For immunoprecipitation used to demonstrate association of baculovirus-expressed S. purpuratus p60 and p80, affinity purified anti-p60 antibodies were covalently crosslinked to protein A Sepharose using 20 mM dimethylpimilidate (Harlow and Lane (1988) supra.). After equilibration in TBST, 20–40 μl of antibody beads were added to katanin samples diluted in TBST containing 1–2 mg/ml soybean trypsin inhibitor (SBTI). The immunoprecipitations were incubated at 4° C. for 1–2 hr, washed five times with 1 ml of ice-cold TBST, and eluted in SDS-containing sample buffer.

Baculovirus Expression and Purification of Katanin

Katanin subunits were expressed using the Bac-to-Bac™ baculovirus expression system (Life Technologies), a commercial version of the site-specific transposition system for making recombinant baculovirus (Luckow et al. (1993) *J. Virology* 67: 4566–4579). p60 and p80 cDNA coding sequences were each PCR amplified (Expand polymerase, Boehringer Mannheim) and then subcloned separately into pFastBac HT, which resulted in the fusion of a 6xHis $Ni^{2+}$ binding sequence to the N-terminus of both p80 and p60. A p60-p80 coexpression virus was made by cloning the complete p60-FastBac HT and p80-FastBac HT coding regions into the transfer vector, pDual. Recombinant baculoviruses were prepared according to the Life Technologies protocol.

Sf9 cells were grown in SFM-900 II SFM (Life Technologies) supplemented with 100x antibiotic/antimycotic (Life Technologies) to 0.5x using the shaker culture method (Weiss et al. (1995) pp. 79–85 in *Baculovirus Expression Protocols*, C. D. Richardson, ed. Totowa, N.J.: Humana Press Inc.). Expression of katanin subunits was performed in 11 flasks containing 200–300 ml of media using a multiplicity of infection of 0.5–1.0 pfu/cell. The cells were harvested at approximately 72 hr post infection by low speed centrifugation and resuspended in lysis buffer (50 mM Tris pH 8.5, 300 mM NaCl, 2 mM $MgCl_2$, 20 mM imidazole, 10 mM 2-mercaptoethanol, 1 mM ATP, 1 µg/ml pepstatin, 1 µg/ml leupeptin, 1 µg/ml aprotinin) before freezing in liquid nitrogen, and storage at –80° C.

To purify the expressed subunits, frozen cells were thawed and DNA was sheared by two passes through a Bio-Neb Cell Disrupter (100 psi helium, 13 1/min). Cell debris was removed by centrifugation (40,000xg for 45 min). Subunits were bound in batch to $Ni^{2+}$-NTA Superflow (QIAGEN), washed [20 mM Tris pH 8.0, 1 M NaCl, 2 mM $MgCl_2$, 40 mM imidazole, 0.02% Triton X- 100, 10 mM 2-mercaptoethanol, 0.5 mM ATP] and eluted [20 mM Tris pH 8.0, 100 mM NaCl, 150 mM imidazole, 2 mM $MgCl_2$, 0.02% Triton X- 100, 10 mM 2-mercaptoethanol, 100 µm ATP], followed by freezing in liquid nitrogen. Additional purification was sometimes performed by anion-exchange chromatography. Katanin concentrations were estimated by comparison with BSA standards using either a commercial Bradford reagent (Bio-Rad) or by densitometric analysis of Coomassie-stained SDS-PAGE gels with NIH-IMAGE after image capture on a CCD-based imaging system (Foto/Analyst, Fotodyne).

Electron Microscopic Imaging

Proteins were adsorbed to mica, freeze-dried, and platinum replicated according to established procedures (Heuser (1989) *J. Electron Microsc. Technique* 13 ):, 244–263; Heuser (1983) *J. Mol. Biol.* 169: 155–195). Sample preparation and imaging were similar to that used in the imaging of NSF (Hanson et al. (1997) *Cell* 90: 523–535), except that mica flakes were washed with a buffer consisting of 10 mM K-HEPES (pH 7.5), 2 mM $MgCl_2$, 1 mM nucleotide (ATP or ATP-γ-S). Images were processed using Adobe Photoshop and displayed at 300,000x.

ATPase Assays

ATPase activity was measured by a modified malachite green method (Kodama et al. (1986) *J. Biochem.* 99: 1465–1472). ATPase reactions of 50–100 µl, were carried out in a buffer previously used for measuring the ATPase activity of native katanin [20 mM K-HEPES pH 8.0, 25 mM potassium glutamate 2 mM $MgCl_2$, 10% glycerol (v/v), 0.02% Triton X-100 (w/v), 1 mg/ml BSA] (McNally and Vale (1993) *Cell*, 75: 419–429), except that soybean trypsin inhibitor (SBTI) was replaced by BSA as a carrier protein because SBTI increased background phosphate contamination. An ATP regenerating system, consisting of 0.5–1.0 mM phosphoenol pyruvate and 2 units of pyruvate kinase, was included to minimize the inhibition by ADP observed previously for native katanin (McNally and Vale (1993) *Cell*, 75: 419–429). Microtubules were prepared from bovine brain tubulin (Hyman et al. (1990) *Meth. Enzymol.* 196: 303–319; and Williams and Lee (1982) *Meth Enzymol.* 85B: 376–385). After assembly, microtubules were sedimented (230,000xg; 10 min), resuspended in ATPase buffer lacking BSA, and the polymers were resuspended by repeated passage through a 27 gauge needle. Microtubule concentration was determined by measuring the absorbance at 275 nm in 6 M guanidine HCl by using a molecular mass of 110 kDa and an extinction coefficient of 1.03 ml $mg^{-1}$ $cm^{-1}$ (Hackney (1988) *Proc. Natl. Acad Sci. USA*, 85: 6314–6318). ATPase reactions were carried out at room temperature, and were initiated by addition of katanin.

Severing Assays

Microscope-based severing assays were performed using previously published procedures (McNally and Vale (1993) *Cell*, 75: 419–429), except that microtubules were immobilized by first perfusing flow cells with a bacterially expressed kinesin mutant that binds strongly to microtubules but is unable to hydrolyze ATP (K560, G234A mutant; R. Vale and E. Taylor, unpublished results). Assays were performed in 20 mM Hepes (pH 7.5), 2 mM $MgCl_2$, 1 mM ATP with an oxygen scavenger system consisting of glucose oxidase (220 µg/ml), catalase (36 µg/ml), glucose (22.5 mM), and 2-mercaptoethanol (71.5 mM). Images were captured using a cooled, slow-scan CCD (Photometerics) and processed using Adobe Photoshop.

DAPI severing assays were performed using conditions where the change in fluorescence intensity was linear with the amount of tubulin polymer added (Heusele et al. (1987) *Eur. J Biochem.* 165: 613–620). Severing reactions containing 2 µM microtubules (polymerized and resuspended in ATPase buffer as above) were incubated with 10 µM DAPI, along with 1 mM ATP, 10 mM phosphoenol pyruvate, 250 µg/ml pyruvate kinase (Boehringer Mannheim), and 1 mg/ml BSA. The reaction volume was 80 µL, and fluorescence intensity was measured by exciting at 370 nm. and measuring the emission at 450 mn using a model 8100 fluorimeter (SLM Instruments) in photon counting mode.

In vitro Translation Co-Immunoprecipitation

In order to facilitate the non-radioactive detection of in vitro translated p60 and p80, each cDNA was ligated into the vector pCITE-4a+ (Novagen) such that the proteins would be translated in frame with a 37 amino acid N-terminal S-Tag. In vitro synthesis of proteins directly from plasmid DNAs was accomplished using the Single Tube Protein System 2, T7 (Novagen). For co-immunoprecipitation assays, p60 and p80 constructs were usually co-expressed. However, identical results were obtained if the constructs were expressed separately and the incubated together for 30 min at room temperature. For immunoprecipitations, lysates were incubated on ice with Pansorbin (Calbiochem)-antibody complexes, washed in NET buffer (50 mM Tris-Cl (pH 7.5), 150 mM NaCl, 0.1% Nonidet P40, 1 mM EDTA (pH 8.0), 0.25% gelatin and 0.02% sodium azide), then resuspended in SDS-PAGE sample buffer. In vitro translation products in both the pellets and supernatants from the immunoprecipitations were resolved by SDS-PAGE, transferred to nitrocellulose, probed with S-protein HRP conjugate (Novagen) and detected by chemiluminescence.

Cell Culture and Transfections and Immunofluorescence

To allow transient expression of a human p80 WD40-GFP fusion protein in HeLa cells, a DNA fragment containing amino acids 1–263 of human p80 katanin was generated by PCR amplification, placing a BamHI site and a Kozak consensus at the predicted translation start and an EcoRI site after the codon for a.a. 263. This BamHI-EcoRI fragment was ligated into the GFP fusion vector pEGFP-N1 (Clontech).

Both MSU1.1 and HeLa cells were grown on 18 mm glass coverslips in Optimem medium (Life Technologies) supplemented with 10% fetal bovine serum, penicillin and streptomycin. Plasmids were transfected using Superfect Reagent (Qiagen) for 2 hr after which coverslips were washed with PBS and placed in fresh culture medium at 37° C. with 5% $CO_2$ for 1–24 hr.

For imaging of GFP-fluorescence and immunofluorescence with the human p80 katanin antibody or with the γ-tubulin antibody, monoclonal GTU88 (Sigma Chemical), cells on coverslips were fixed either in −20° C. methanol or in 0.5× PBS, 3.7% formaldehyde, 75% methanol at 22° C. for 10 min followed by rehydration in TBST. Antibody labelling was carried out in TBST containing 4% BSA. Images were captured with a Nikon Microphot SA microscope, 100× Plan Fluor 1.3 objective, Photometrics Quantix camera and IP Lab Spectrum software (Scanalytics).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polypeptide having microtubule severing activity, said polypeptide comprising an isolated p60 subunit of katanin encoded by a nucleic acid that hybridizes with the complement of a nucleic acid that encodes the polypeptide of SEQ ID NO:1, when incubated in 50% formamide for about 8 to 16 hours at 42° C.

2. The polypeptide of claim 1, wherein said polypeptide is the polypeptide of SEQ ID NO:1 or the polypeptide of SEQ ID NO:1 having conservative substitutions.

3. The polypeptide of claim 1, wherein:
said polypeptide, when presented as an antigen, elicits the production of an antibody that specifically binds to a polypeptide sequence as set forth in SEQ ID NO:1; and
said polypeptide does not bind to antisera raised against a polypeptide as set forth in SEQ ID NO:1, that has been fully immunosorbed with a polypeptide as set forth in SEQ ID NO:1.

4. The polypeptide of claim 1, wherein said polypeptide is the polypeptide of SEQ ID NO:1.

* * * * *